US010758357B2

(12) United States Patent
Jansen

(10) Patent No.: US 10,758,357 B2
(45) Date of Patent: Sep. 1, 2020

(54) JOINT SPACER

(71) Applicant: REVOMOTION GMBH, Cologne (DE)

(72) Inventor: Josef Jansen, Bergisch Gladbach (DE)

(73) Assignee: REVOMOTION GMBH, Cologne (DE)

( * ) Notice: Subject to any disclaimer, the term of this patent is extended or adjusted under 35 U.S.C. 154(b) by 545 days.

(21) Appl. No.: 15/028,681

(22) PCT Filed: Oct. 9, 2014

(86) PCT No.: PCT/DE2014/100354
§ 371 (c)(1),
(2) Date: Apr. 11, 2016

(87) PCT Pub. No.: WO2015/051785
PCT Pub. Date: Apr. 16, 2015

(65) Prior Publication Data
US 2016/0256285 A1    Sep. 8, 2016

(30) Foreign Application Priority Data

Oct. 11, 2013 (DE) .................. 10 2013 016 899
Nov. 19, 2013 (DE) .................. 20 2013 010 444 U

(51) Int. Cl.
*A61F 2/38* (2006.01)
*A61L 27/18* (2006.01)
(Continued)

(52) U.S. Cl.
CPC ........ *A61F 2/3872* (2013.01); *A61F 2/30756* (2013.01); *A61F 2/32* (2013.01); *A61L 27/165* (2013.01); *A61L 27/18* (2013.01); *A61L 27/50* (2013.01); *A61L 27/56* (2013.01); *A61F 2/34* (2013.01); *A61F 2/36* (2013.01); *A61F 2002/3008* (2013.01);
(Continued)

(58) Field of Classification Search
CPC .......... A61F 2/3872; A61F 2002/30757; A61F 2002/3895
See application file for complete search history.

(56) References Cited

U.S. PATENT DOCUMENTS 5,133,742 A   7/1992   Pinchuk
5,545,229 A   8/1996   Parsons et al.
(Continued)

FOREIGN PATENT DOCUMENTS

DE      10243966     4/2004
WO       9820939     5/1998
(Continued)

OTHER PUBLICATIONS

Geary et al. Journal of Materials Science: Materials in Medicine, 2008, vol. 19, Nr:11, pp. 3355-3363, Kluwer Academic Publishers, Bo—ISSN 1573-4838, "Characterisation of Bionate polycarbonate polyurethanes for orthopaedic applications".
(Continued)

*Primary Examiner* — Megan Y Wolf
(74) *Attorney, Agent, or Firm* — Brooks Kushman P.C.

(57) ABSTRACT

A joint spacer, in particular a knee spacer and a hip spacer is provided which is long-lasting and is sufficiently cushioned and abrasion-resistant and which can also support locally very high loads.

14 Claims, 30 Drawing Sheets

Figure 1:
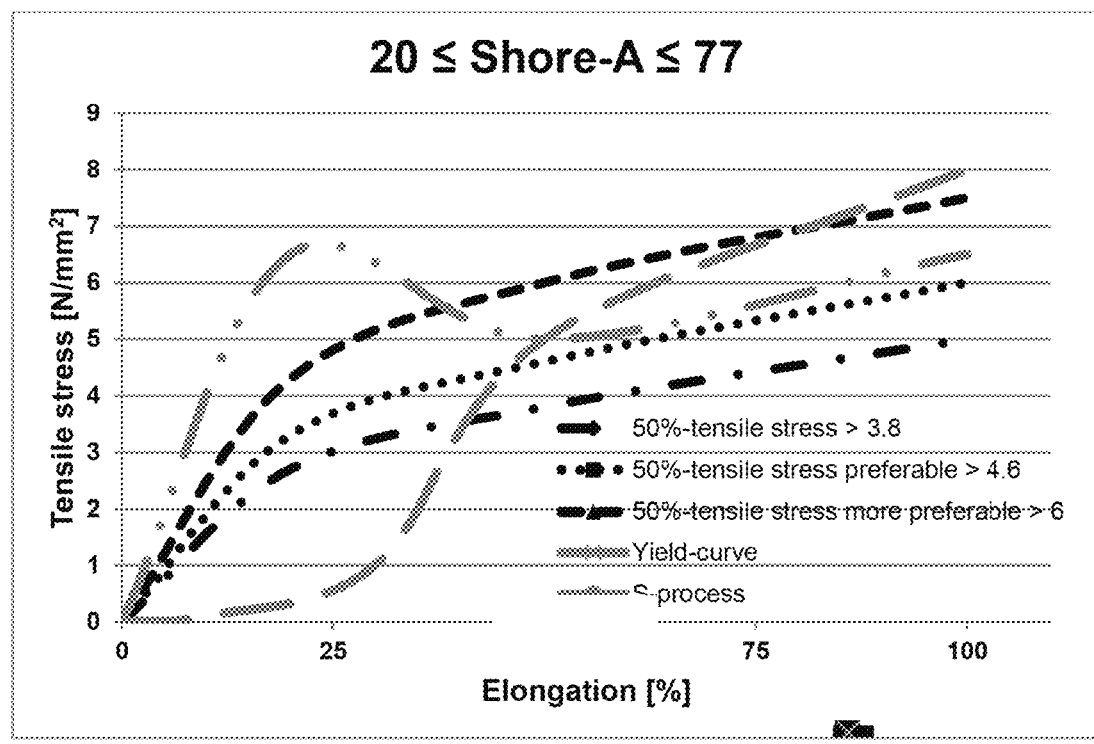

(51) Int. Cl.

| | | |
|---|---|---|
| *A61L 27/16* | (2006.01) | |
| *A61L 27/56* | (2006.01) | |
| *A61L 27/50* | (2006.01) | |
| *A61F 2/30* | (2006.01) | |
| *A61F 2/32* | (2006.01) | |
| *A61F 2/44* | (2006.01) | |
| *A61F 2/36* | (2006.01) | |
| *A61F 2/46* | (2006.01) | |
| *A61F 2/34* | (2006.01) | |

(52) U.S. Cl.
CPC ............ *A61F 2002/30016* (2013.01); *A61F 2002/3092* (2013.01); *A61F 2002/30467* (2013.01); *A61F 2002/30576* (2013.01); *A61F 2002/30594* (2013.01); *A61F 2002/30757* (2013.01); *A61F 2002/30878* (2013.01); *A61F 2002/30909* (2013.01); *A61F 2002/30971* (2013.01); *A61F 2002/4495* (2013.01); *A61F 2002/4631* (2013.01); *A61L 2430/02* (2013.01); *A61L 2430/06* (2013.01); *A61L 2430/24* (2013.01)

(56) References Cited

U.S. PATENT DOCUMENTS

| | | | |
|---|---|---|---|
| 5,993,972 | A | 11/1999 | Reich et al. |
| 6,140,452 | A | 10/2000 | Felt et al. |
| 7,087,083 | B2 | 8/2006 | Pasquet |
| 7,766,965 | B2 | 8/2010 | Bao et al. |
| 8,962,785 | B2 | 2/2015 | Faust et al. |
| 2003/0093152 | A1 | 5/2003 | Pedersen |
| 2005/0171604 | A1* | 8/2005 | Michalow ............... A61F 2/38 623/14.12 |
| 2007/0027285 | A1 | 2/2007 | Gunatillake |
| 2007/0067032 | A1* | 3/2007 | Felt .................... A61B 17/1675 623/14.12 |
| 2007/0100450 | A1* | 5/2007 | Hodorek ............. A61F 2/30721 623/14.12 |
| 2007/0233268 | A1 | 10/2007 | Wagner |
| 2008/0097606 | A1 | 4/2008 | Cragg et al. |
| 2008/0208346 | A1* | 8/2008 | Schwartz ............. A61B 17/562 623/17.17 |
| 2009/0043398 | A1* | 2/2009 | Yakimicki ............. A61F 2/3094 623/23.51 |
| 2009/0234453 | A1 | 9/2009 | Steinberg |
| 2010/0039690 | A1* | 2/2010 | Agrawal ................... G02F 1/15 359/265 |
| 2010/0179298 | A1* | 7/2010 | Faust ...................... A61L 27/18 528/75 |
| 2011/0206878 | A1* | 8/2011 | Sullivan ................... C08L 27/16 428/36.9 |
| 2013/0211529 | A1 | 8/2013 | Frauens et al. |
| 2013/0218275 | A1 | 8/2013 | Caballes |
| 2013/0312897 | A1* | 11/2013 | Vowles .............. A61B 17/0401 156/83 |
| 2014/0222149 | A1* | 8/2014 | Amis .................... A61F 2/3872 623/14.12 |
| 2014/0277451 | A1* | 9/2014 | Ganz .................... A61F 2/3872 623/14.12 |

FOREIGN PATENT DOCUMENTS

| | | |
|---|---|---|
| WO | 2004029122 A1 | 4/2004 |
| WO | 12083366 A1 | 6/2012 |
| WO | 12106763 A1 | 8/2012 |

OTHER PUBLICATIONS

International Search Report for PCT/DE2014/100354, English Translation attached to original, Both completed by the European Patent Office on Feb. 19, 2015, All together 7 Pages.

C. Geary et al., J Mater Sci: Mater Med, Characterisation of Bionate polycarbonate polyurethanes for orthopaedic applications vol. 19, 2008, pp. 3355-3363.

Jones E et al: "Compliant-layer tibial bearing inserts: Friction testing of different materials and designs for a new generation of prostheses that mimic the natural joint", Proceedings of the Institution of Mechanical Engineers.Journal of Engineering in Medicine. Part H, Mechanical Engineering Publications Ltd, London, GB, vol. 222, No. 8, Jan. 2008 (Jan. 1, 2008), pp. 1197-1208.

Ong et al: "New Biomaterials for Orthopedic implants", Orthopedic Research and Reviews, vol. 2015-7, Sep. 8, 2015 (Sep. 8, 2015), pp. 107-130.

"PUR Elastomere": Retrieved from the Internet <URL:http://www.mattec.at/Polyurethaninfo.htm> [retrieved on Jun. 5, 2018].

Herrlinger et al.: Houben-Weyl, Methoden der organischen Chemie, vol. 24/2, Jan. 7, 1963, Georg Thieme Verlag, Stuttgart, article E.Müller: Kautschukelastische Stoffe, pp. 79-81, XP055481377.

Vieweg et al. Kunststoff-Handbuch vol. VII 1966 Carl Hanser Verlag, München article Ellegast, Konrad Wasservemetzte Produkte, pp. 270-273.

* cited by examiner

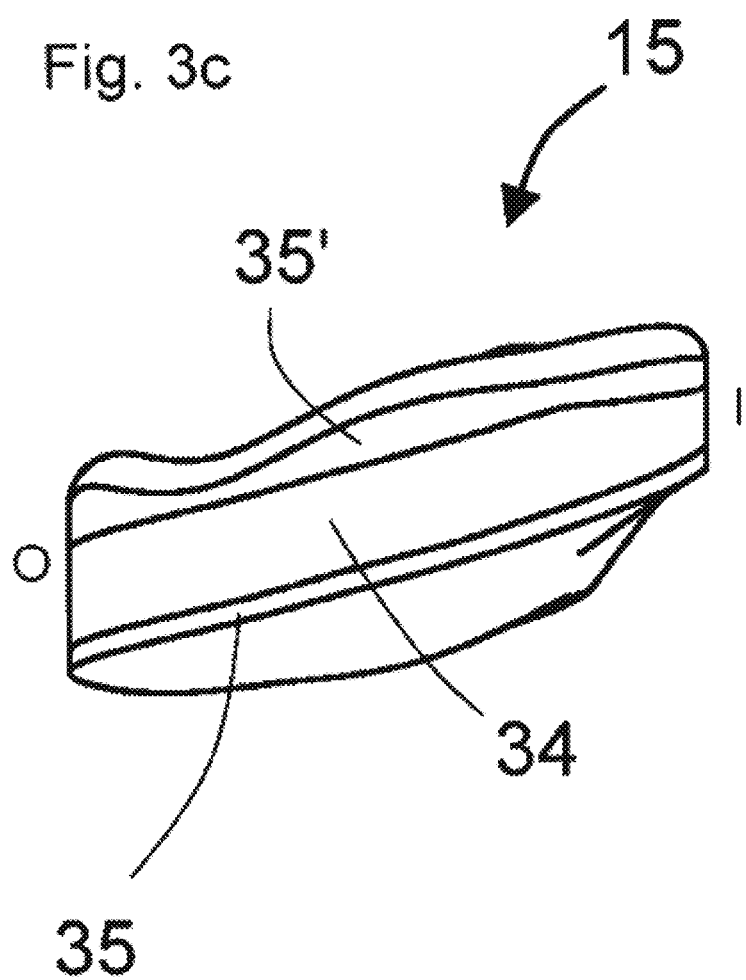

Figure 3B:
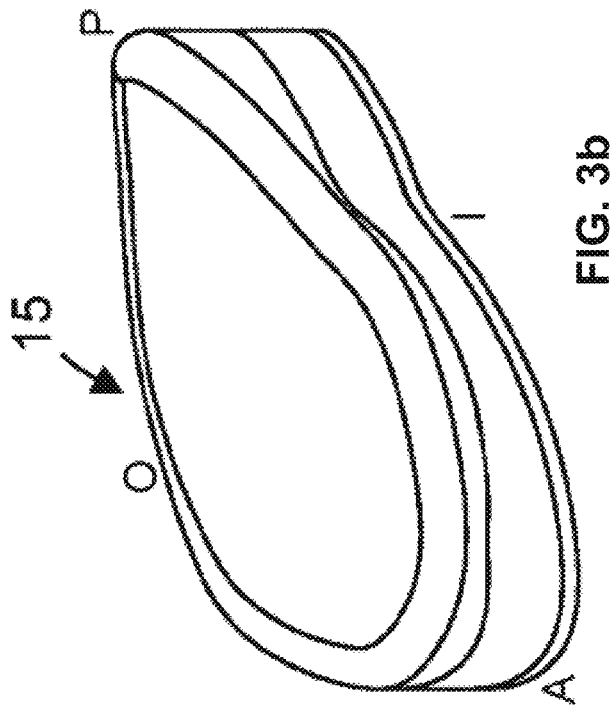

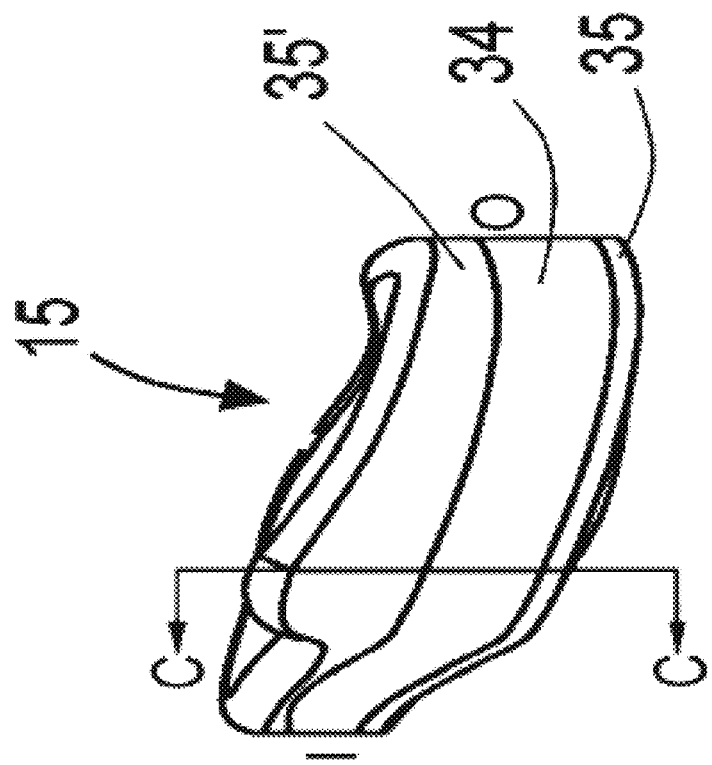
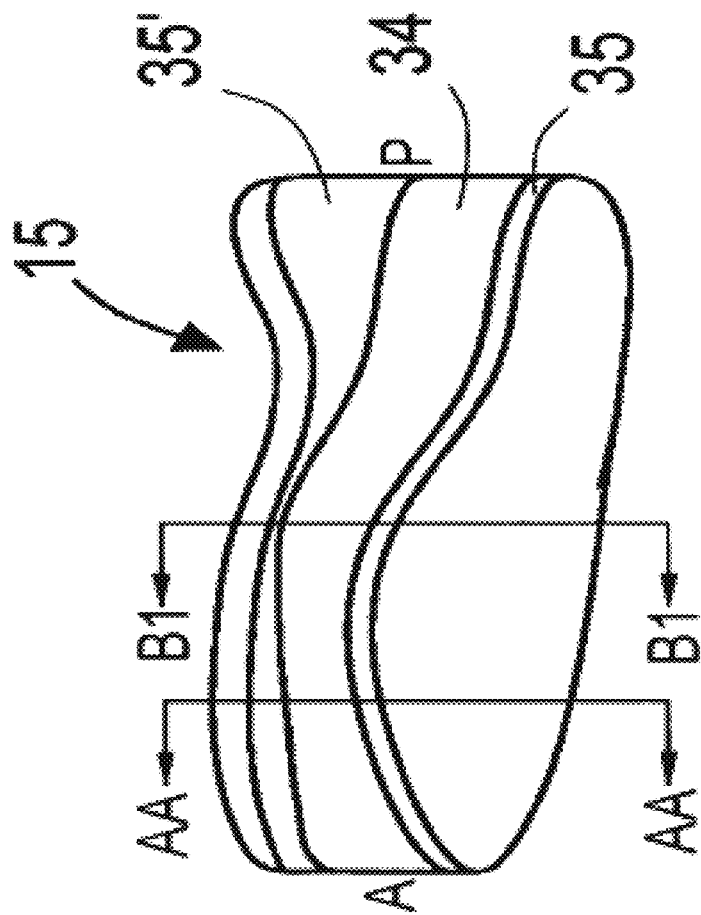
FIG. 3e
FIG. 3d

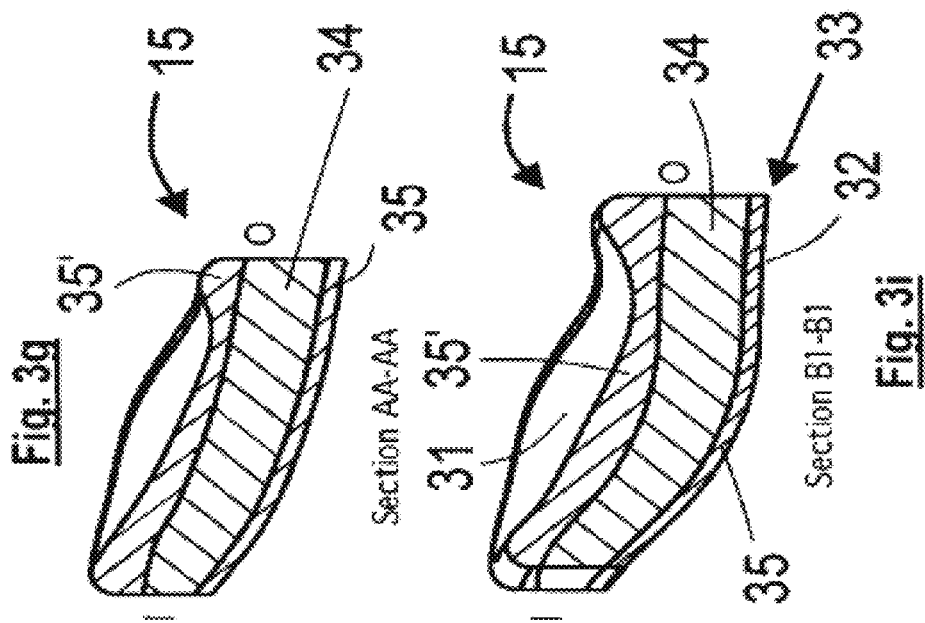
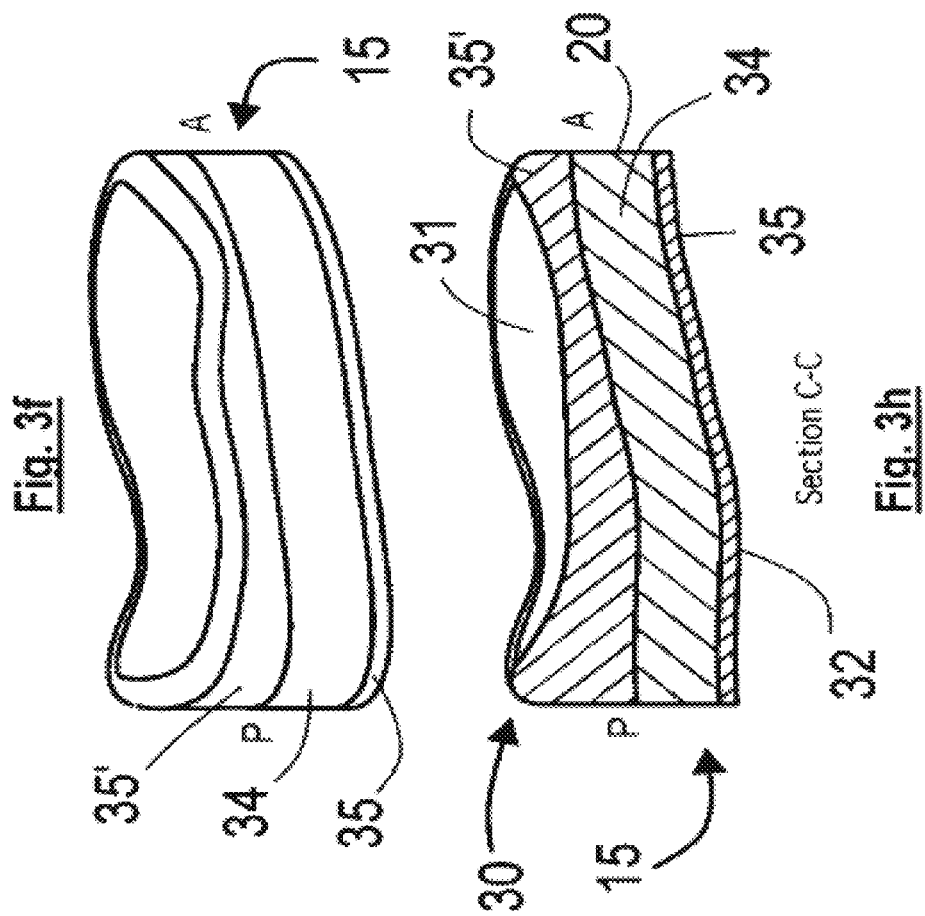

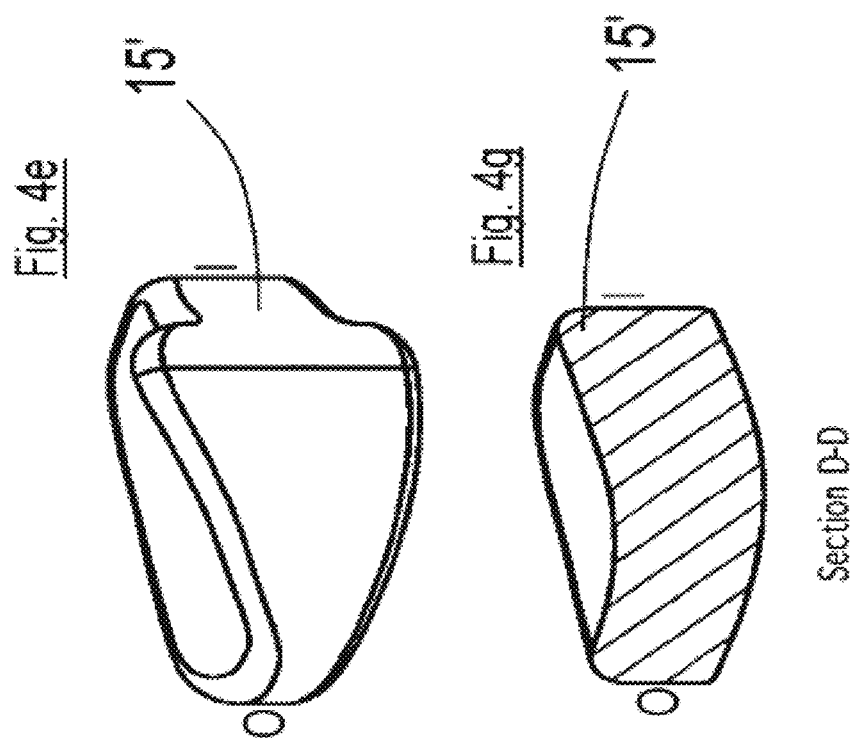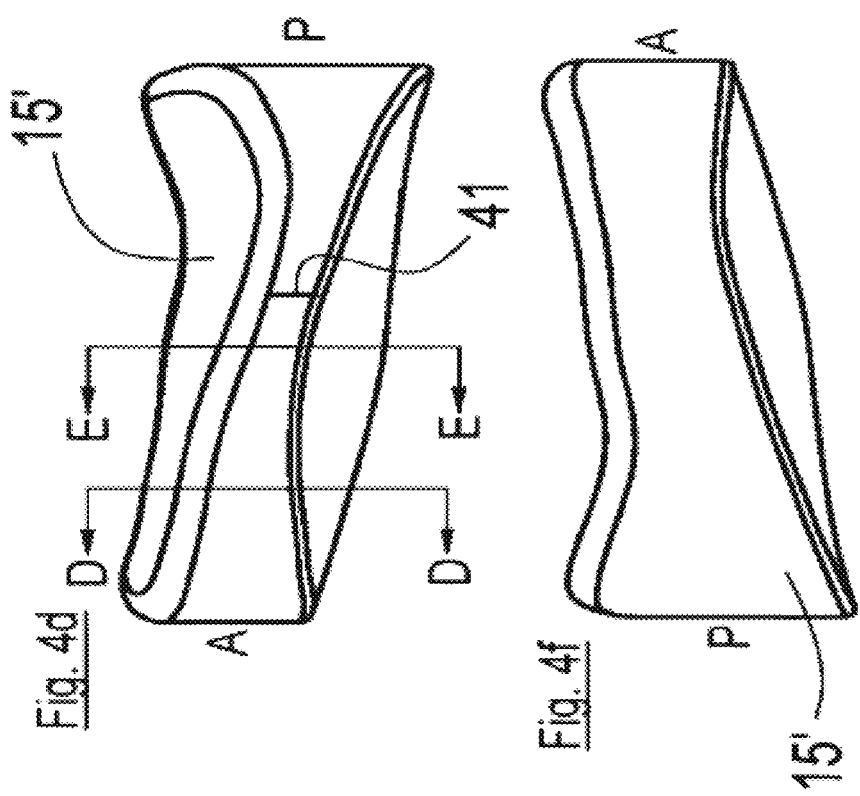

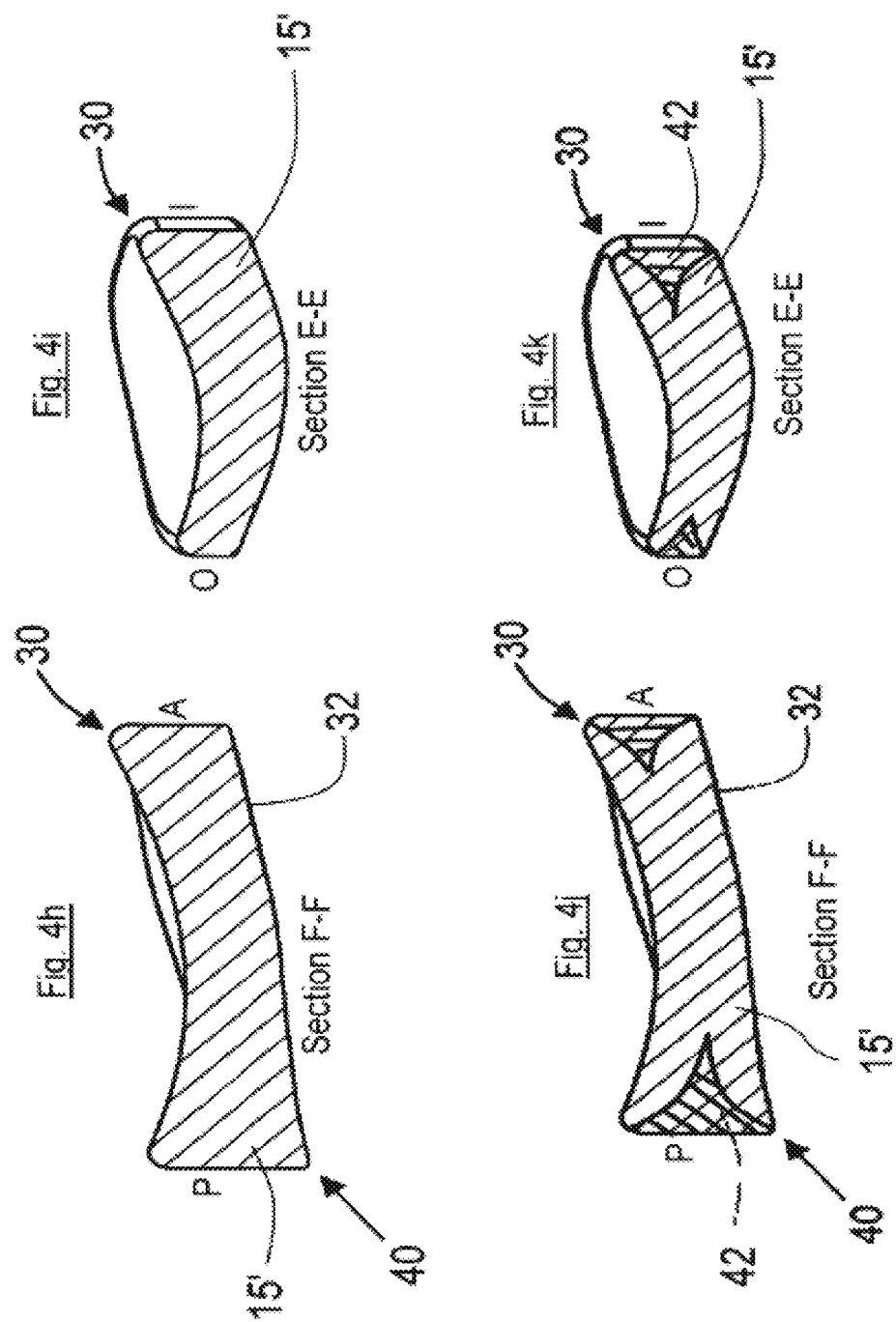

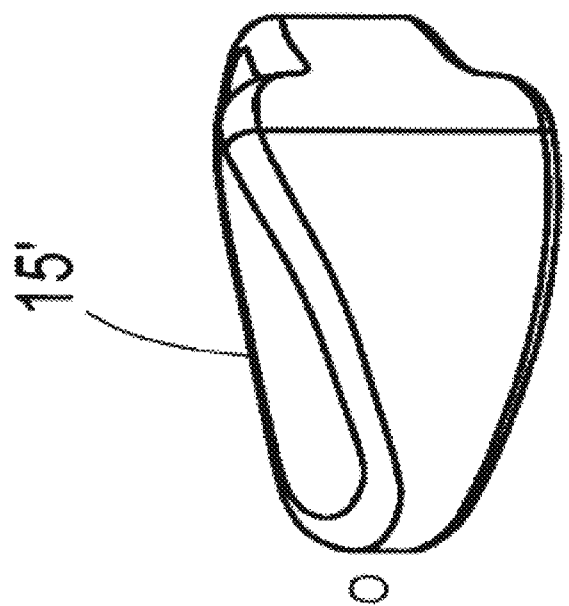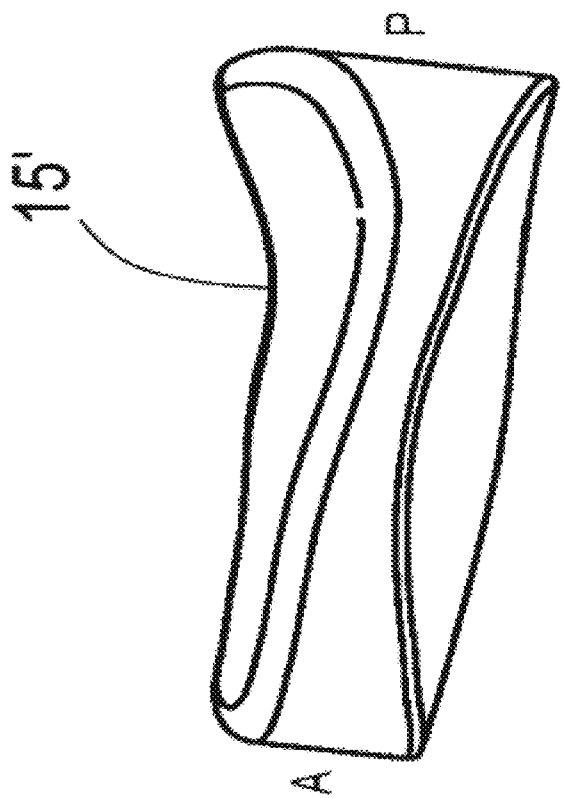

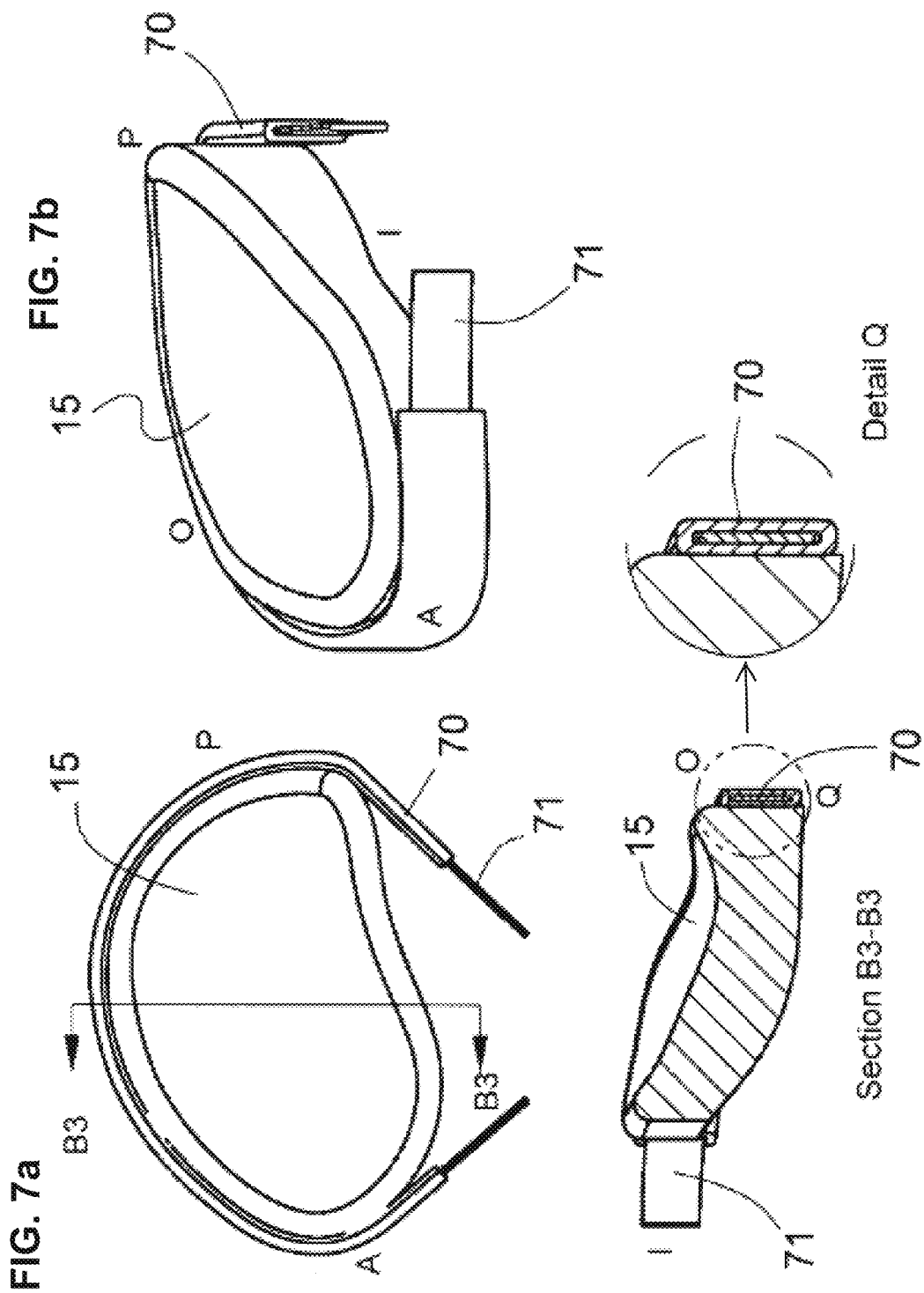

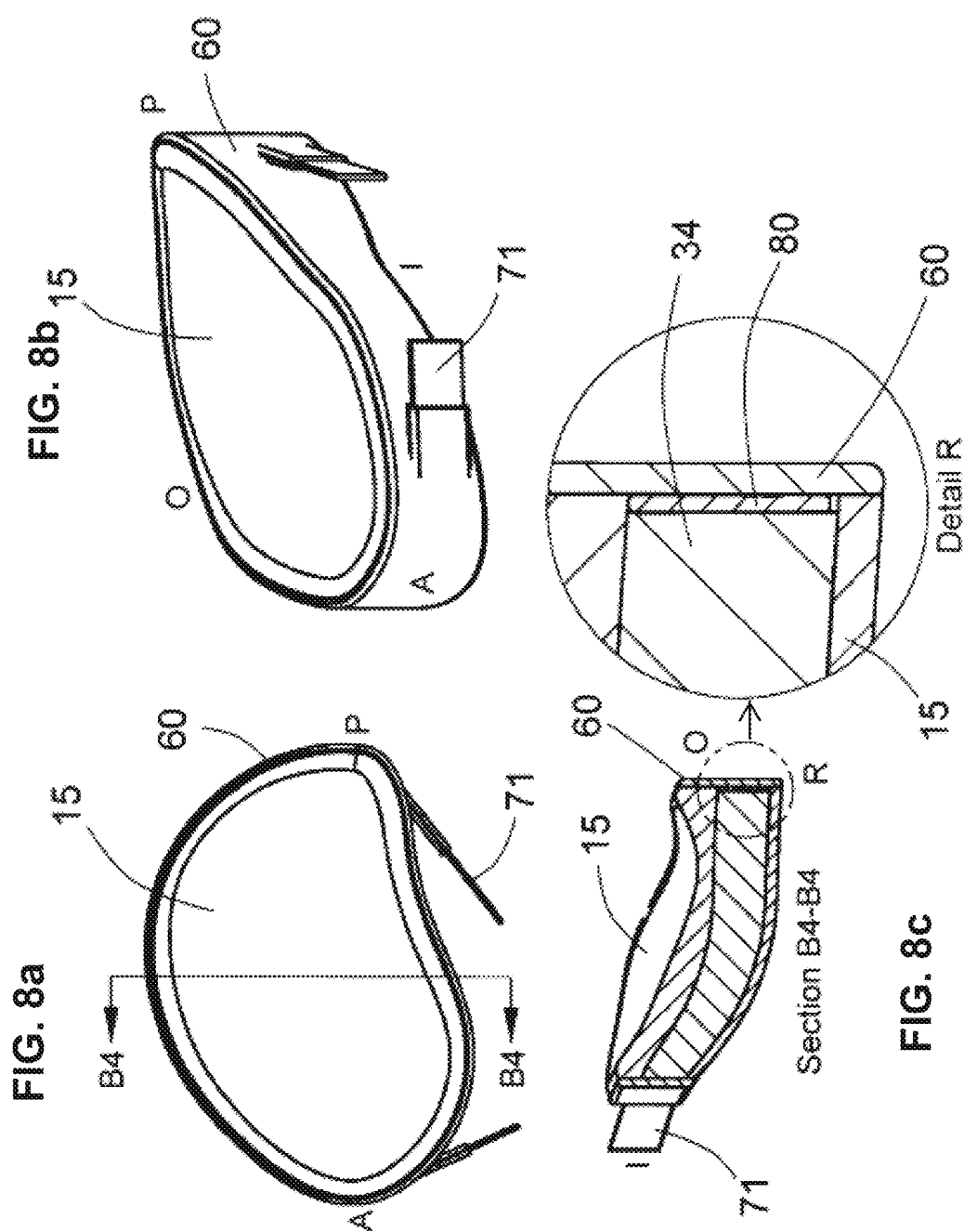

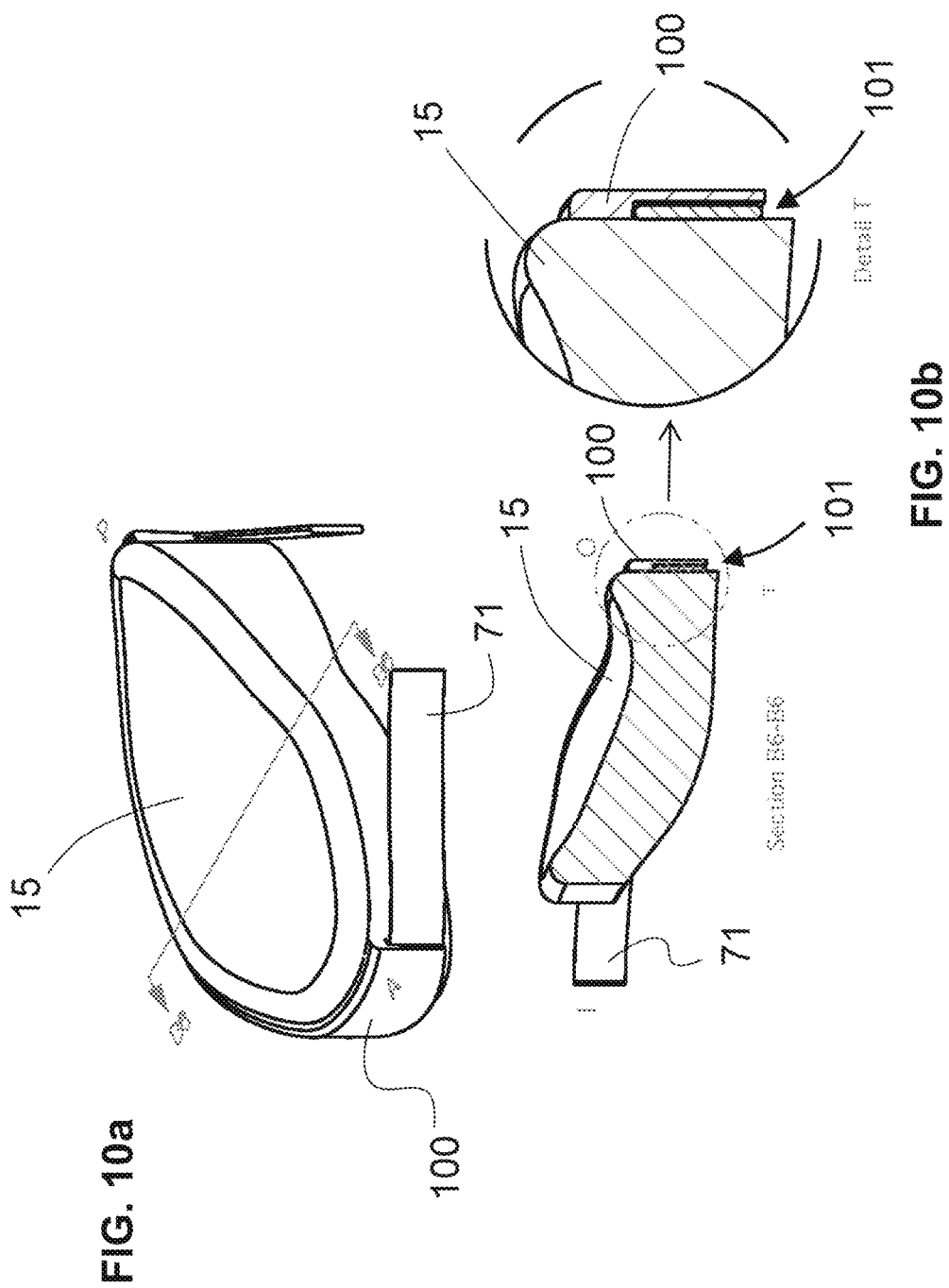

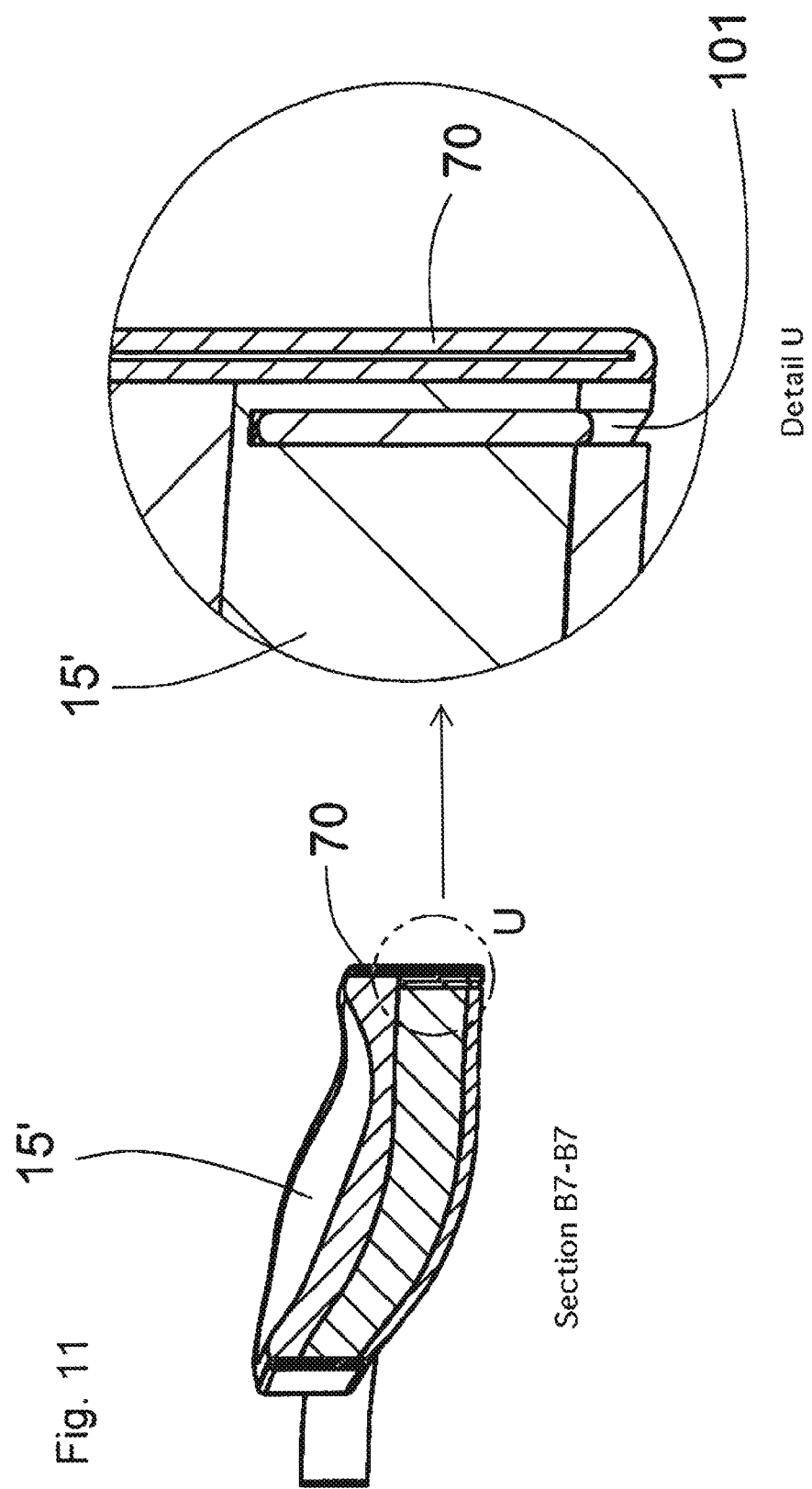

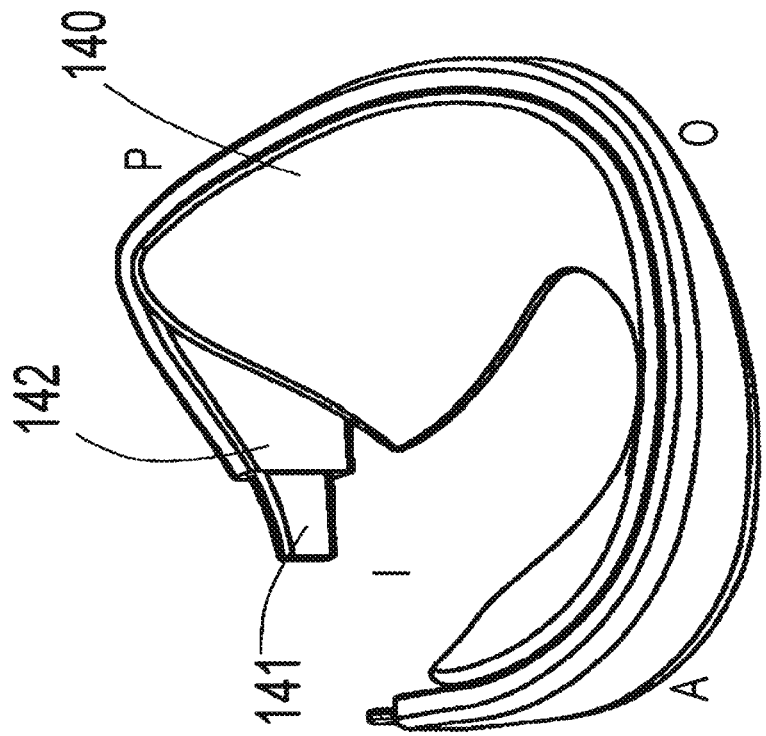
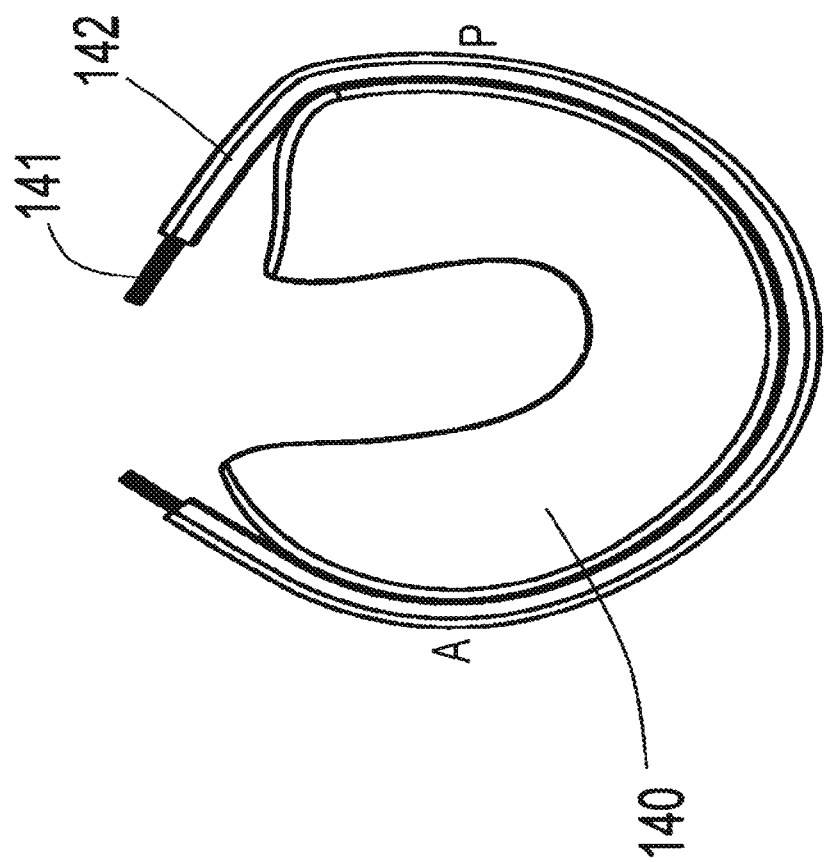
FIG. 14b
FIG. 14a

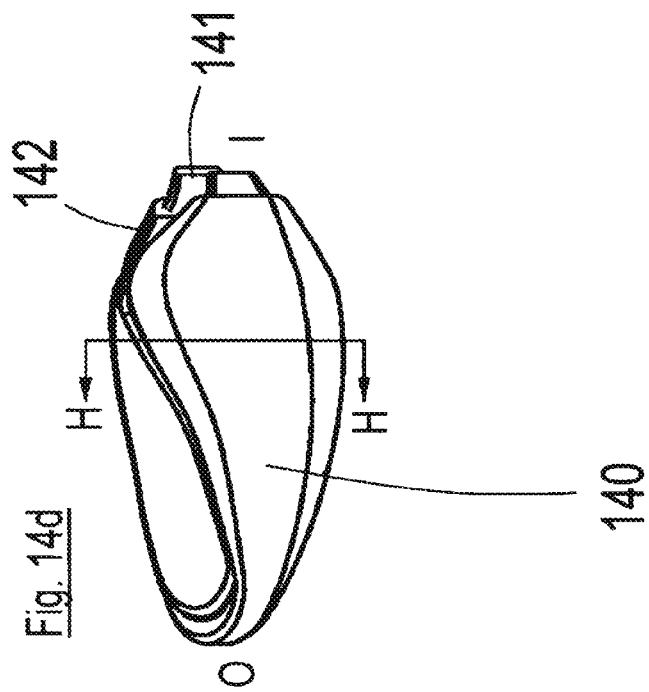
Fig. 14d
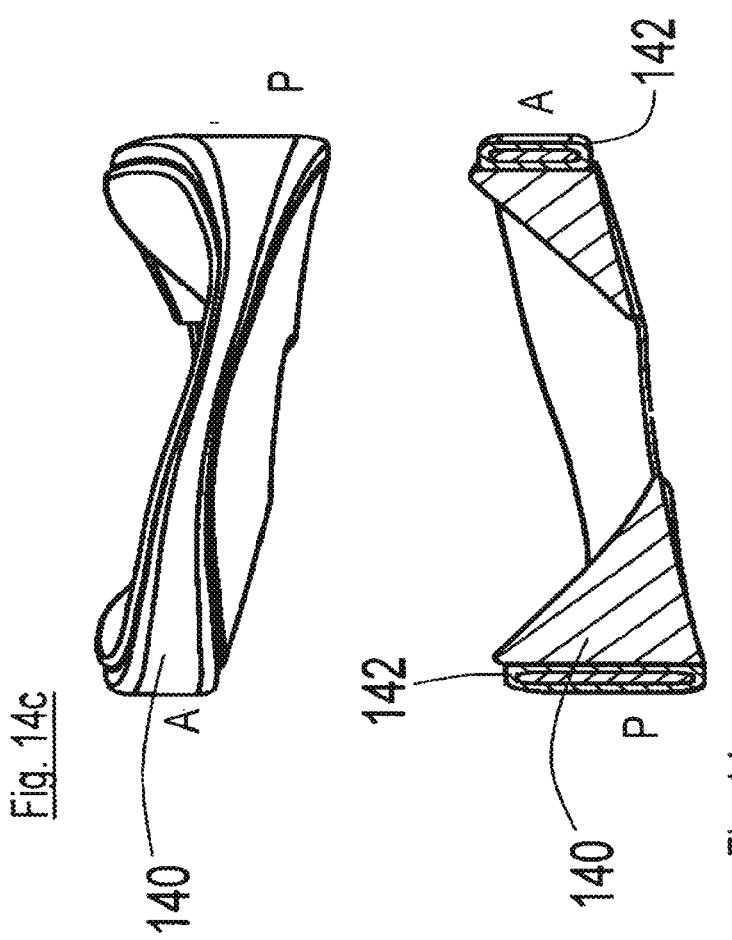
Fig. 14c
Fig. 14e
Section H-H

FIG. 15a
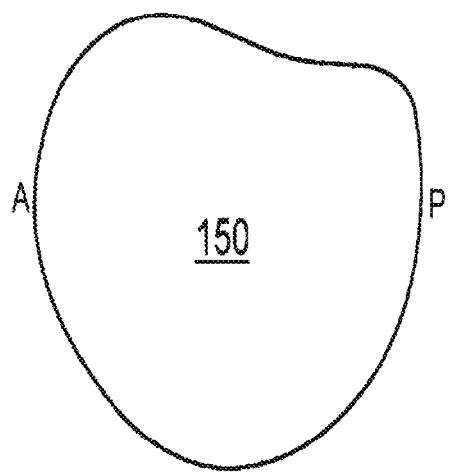
FIG. 15b
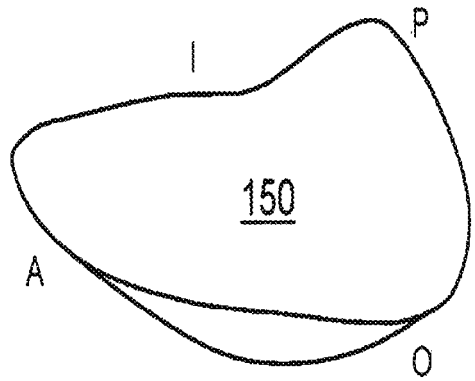
FIG. 15c
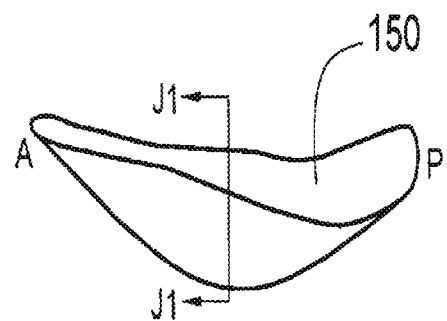
FIG. 15d
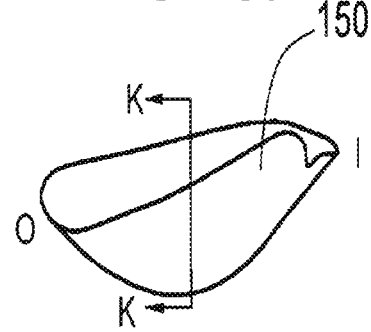
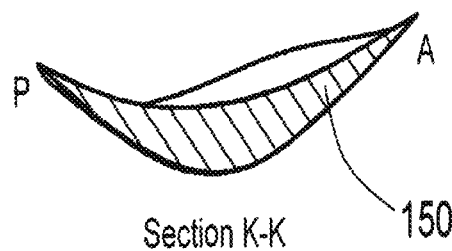
Section K-K
FIG. 15e
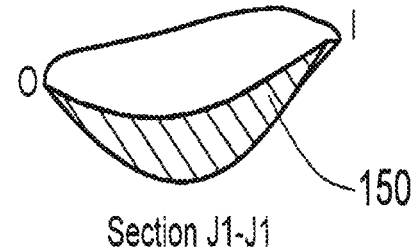
Section J1-J1
FIG. 15f

FIG. 18a
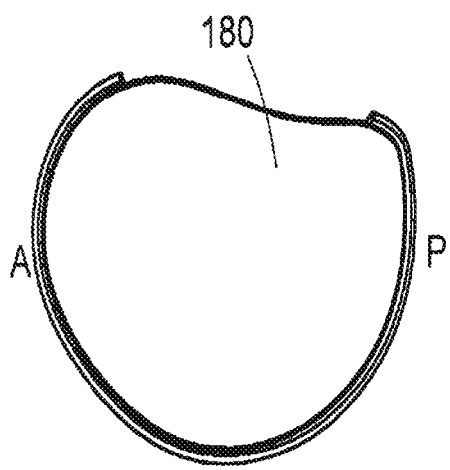
FIG. 18b
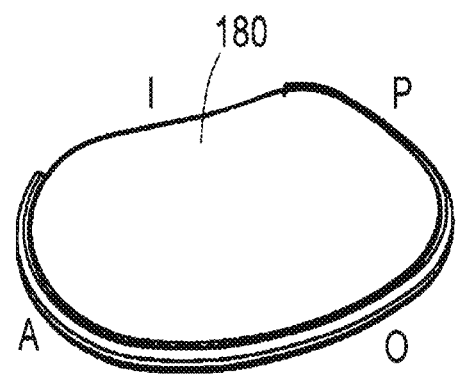
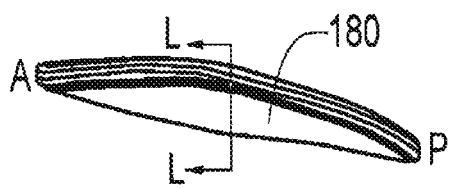
FIG. 18c
FIG. 18d
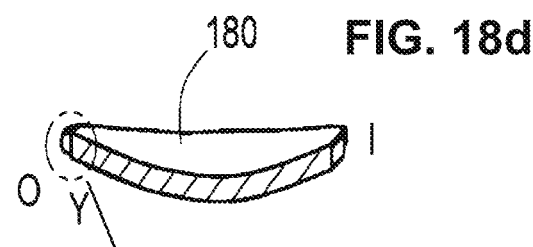
Section L-L
FIG. 18e
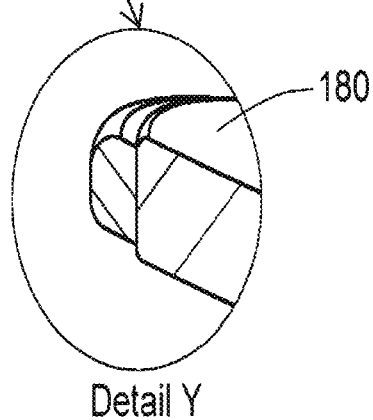
Detail Y

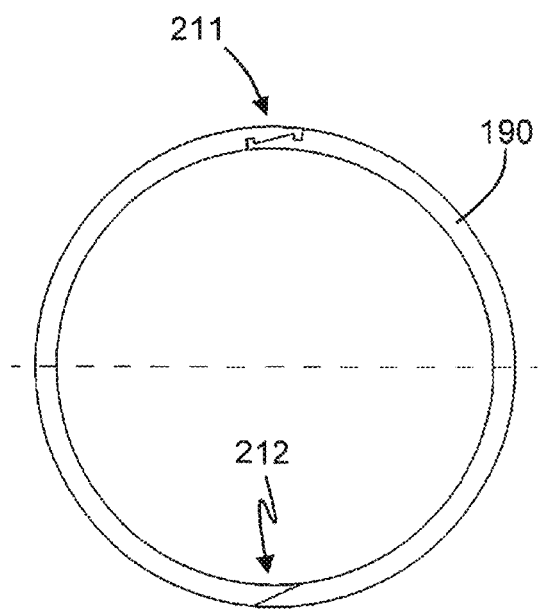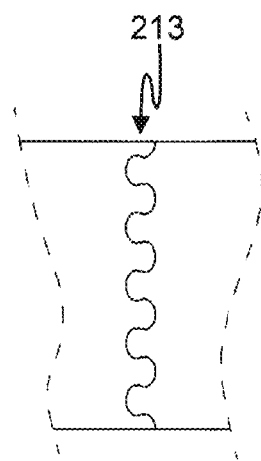
FIG. 21a
FIG. 21b

JOINT SPACER

CROSS-REFERENCE TO RELATED APPLICATION

This application is the U.S. national phase of PCT Application No. PCT/DE2014/100354 filed on Oct. 9, 2014, which claims priority to DE Patent Application No. 10 2013 016 899.6 filed on Oct. 11, 2013 and, DE Patent Application No. 20 2013 010 444.9 filed on Nov. 19, 2013, the disclosures of which are incorporated in their entirety by reference herein.

The invention concerns a joint spacer, in particular a knee spacer and a hip spacer.

In order to produce a long-lasting joint spacer which is sufficiently cushioned and abrasion-resistant, and which can also support locally very high loads, the invention proposes a joint spacer having a Shore-A hardness of between 20 and 77 and tensile stress values at unit strain of between 20% and 60%, preferably 50%, of greater than 3.8 N/mm², preferably greater than 4.6 N/mm² and particularly preferably greater than 6 N/mm², and/or compressive stress values at linear compression of between 20% and 60%, preferably 50%, of greater than 7.8 N/mm², preferably of greater than 9 N/mm², and particularly preferably of greater than 10.5 N/mm², and/or a Shore-A hardness of up to 85 and tensile stress values at unit strain of between 20% and 60%, preferably 50%, of greater than 6 N/mm², preferably of greater than 7 N/mm², and particularly preferably of greater than 8 N/mm², and/or compressive stress values at linear compression of between 20% and 60%, preferably 50%, of greater than 10.5 N/mm², preferably of greater than 12 N/mm², and particularly preferably of greater than 14 N/mm².

DESCRIPTION

Joint Spacer

The present invention concerns a joint spacer, particularly a knee spacer and a hip spacer.

Millions of people worldwide are affected with osteoarthritis, the premature wear and tear of cartilaginous joint surfaces, mostly in the knees and hip. As an alternative to the previous artificial joints (endoprosthesis) associated with various disadvantages, elastic, disc-shaped spacers called "knee spacers" are available. These can be introduced in the interior of the knee with the help of a small skin incision after the removal of the (remaining) meniscus, by smoothing the joint surfaces and by selecting the size carefully. In the joint, they replace the worn out cartilage and the damaged meniscus. The knee spacers restore the natural joint space and can therefore, also correct deformities such as X or O misalignments (valgus, varus) of the leg.

The natural medial (inner) and lateral (outer) menisci are crescent-shaped fibrocartilage tissues that are wedge-shaped cross-sectionally and are anchored through the anterior and posterior horns in the tibial plateau. They increase the contact area between the tibial plateau and the joint rollers (condyles) of the femur (thigh bone).

Joint spacers generally denote spacers that can be used in other joints of the human body such as the hip, the shoulder, the foot, the hand or the vertebrae. Joint spacers here also include "plugs" or flat plugs which can replace only a small part of the cartilage surface of a joint. In addition, spacers are used as lubricating and damping elements for endoprostheses. In knee spacers one distinguishes between different embodiments. The meniscus spacer replaces the meniscus and worn out cartilage of the joint surfaces, but the meniscal implant replaces only the meniscus. The joint surface replacement or joint surface spacer compensates the partially worn out cartilage or the initial wear of the joint surfaces without replacing the meniscus.

It is known that a knee spacer can consist of different materials and polymers. Here polyurethanes are very suitable because of their high mechanical strength and high abrasion resistance. Basically, one can distinguish between aromatic and aliphatic polyurethanes. Aromatic polyurethanes usually have greater mechanical strength and therefore seem more appropriate for the high loads that occur in a knee spacer during flexion and extension. Compared to aliphatic polyurethanes, aromatic polyurethanes have the disadvantage that they lead to "yellowing", and therefore show a certain amount of aging effect. In addition, aromatic polyurethanes are also controversial because their potential degradation products can have a carcinogenic risk.

Knee spacers have not been successful in practice thus far because the implants often break, slip out of the joint space of the knee or impose motion restrictions. In particular, knee spacers with physiological damping coupled with adequate mechanical strength and fatigue strength are not known currently. Physiological damping is however desirable, because it leads to an absence of pain in the patient.

The task of the present invention is to provide a durable, abrasion-resistant and sufficiently damped joint spacer which can also selectively absorb very high loads. The joint spacer should also achieve maximum congruence between the articulating joint surfaces and should not slip out of the joint space.

This task is achieved by the joint spacer according to claim 1. According to the invention therefore, the joint spacer consists at least partially of a material, in particular an elastomer or thermoplastic elastomer having a Shore-A hardness between 20 and 77 and tensile stress values at elongations between 20% and 60%, preferably 50% (referred to hereafter as 50%-tensile stress), greater than 3.8 N/mm², preferably greater than 4.6 N/mm² and more preferably greater than 6 N/mm², and/or a Shore-A hardness up to 85 and tensile stress values at elongations between 20% and 60%, preferably 50%, greater than 6 N/mm², preferably greater than 7 N/mm² and more preferably greater than 8 N/mm². It is to be noted here stress value at a particular elongation does not mean the tangent or secant modulus. The material should also preferably have no yield behaviour up to 50% elongation, preferably up to 70% elongation.

Preferably, the material should have at a Shore-A hardness between 20 and 77 tensile stresses at 100% elongation (100%-tensile stress) of at least 5 N/mm², preferably at least 6 N/mm² and more preferably at least 7.5 N/mm², or at a Shore-A hardness of up to 85 tensile stress values at 100% elongation of at least 7.5 N/mm², preferably at least 8.5 N/mm² and more preferably at least 10.5 N/mm².

Another characteristic of suitable materials are the compressive stresses, even if the damage to the material is caused significantly more by the occurring tensile stresses. According to the invention therefore, the joint spacer consists at least partially of a material with a Shore-A hardness between 20 and 77 and compressive stress values at compressions between 20% and 60%, preferably 50% (referred to hereafter as 50%-compression stress), greater than 7.8 N/mm², preferably greater than 9 N/mm² and more preferably greater than 10.5 N/mm², and/or a Shore-A hardness of up to 85 and compressive stress values at compressions between 20% and 60%, preferably 50%, greater than 10.5

$N/mm^2$, preferably greater than 12 $N/mm^2$ and more preferably greater than 14 $N/mm^2$.

Such a joint spacer exhibits a distinct progressive pressure-compression behavior advantageously. Elasticity falls disproportionately with increasing compression and the joint spacer therefore becomes harder. In other words, the material is relatively soft in terms of its Shore hardness and has a relatively high modulus of elasticity transversely to the compression at the same time.

The stress values mentioned above can be achieved at lower strain or compression values than the given values, even if the joint spacer is not compressed so strongly at the same loads.

Shore hardness is frequently used to select suitable materials and polymers for joint spacers. Among the known suitable materials for medical technology, the very high loads occurring in the joints, especially in the knees and hips can be absorbed only by materials with a Shore-A hardness above 85. For a high congruence and damping and thus eventually pain relief for the patient however, joint spacers made of such materials would be too hard and therefore less suitable for the knee. The softer the joint spacer, the greater the contact area between joint spacer and articular surface and the smaller the stress, and thus also smaller the abrasion in the joint spacer. In its compliance, the joint spacer should ideally be closer to the natural articular cartilage. This includes the weakened osteoarthritic articular cartilage, so that if possible, it may not be damaged further by the implant. A Shore-A hardness range of 20 to 77, preferably from 45 to 72 is attempted for the material. For very heavy people of about 100-120 kg, the Shore-A hardness of the material should be up to 85, depending on the size of the tibial surface and the joint spacers. Materials, primarily elastomers or thermoplastic elastomers are ideal in this context. The known flexible polymers or other materials in this hardness range cannot build up enough stress at higher deformations to withstand the forces that occur in the joints, i.e., the carrying capacity of the supporting material is not adequate. It has been proven in trials however, that materials which exhibit a pronounced progressive pressure-compression behaviour are suitable for joint spacers. Materials at the same Shore-A hardness can have different modulus of elasticity, and especially establish different levels of stress at a given elongation or compression. In other words, the material is compressed less or more under a predetermined load with the same Shore-A hardness.

Materials, especially elastomers and thermoplastic elastomers can soften with rise in temperature, after absorption of water and after storage in water lasting several months, or under multiple loads (stress-induced softening or so-called Mullins effect; Geary C et al. Characterisation of Bionate Polycarbonates Polyurethanes for Orthopaedic Applications J Mater Sci: Mater Med 19 (2008) 3355-3363). In addition, the mechanical properties change due to sterilization. Besides, materials may solidify at very high test speeds. Therefore, the parameters specified in this invention relate to the testing of samples in a conditioned state at 37° C. after ingestion of water or synovial fluid and at the usual test speeds of the relevant standards in a sterilized state. The stress values are preferably determined after the 5th cycle to compensate the Mullins effect, because the amount of hysteresis can vary considerably, especially in the first few cycles. In addition, the values given above should be reached or exceeded after at least 5 months of storage in water. The materials should therefore be hydrolytically stable. More generally, the materials used should maintain the parameters even after prolonged implantation in the body.

As indicated earlier, softer materials cannot generally withstand the loads occurring in the joints. In addition to the above-described tensile stress values at 50%—or even 100% elongation and 50%-compression stresses, the tear propagation resistance is another important material parameter. The softer the material, the higher should be the tear resistance ideally. In other words it is inversely proportional to the Shore-A hardness. Reference values of this relation are: at a Shore-A hardness of 55, the tear resistance should be greater than 60 N/mm (preferably greater than 70 N/mm), at a Shore-A hardness of 75 greater than 35 N/mm (preferably greater than 40 N/mm). A linear run should exist across these Shore-A hardness ranges over these reference values. The tear propagation resistance relates to sample forms in accordance with the "Trouser Tear test".

The preferred embodiments of the invention are described in the claims and descriptions given below.

Suitable materials for the joint spacer are biocompatible and elastic, durable polymers and here, as already mentioned, the class of polyurethanes in particular. However, other materials such as silicones, PTFE, polysulfone, polyvinyl alcohol, poly(styrene-block-isobutylene-block-styrene) (SIBS), hydrogenated Styrene-block-copolymers (SBS, SIS, SEBS), or other polymers according to the state-of-the-art may also be used. Moreover, in addition to various rubbers, silk or artificial silk is also suitable for joint spacers. It may also be noted that materials with high water absorption in the order of 100% and more are suitable materials for joint spacers. Further, the polymers should be as free from low-molecular components as possible, so that the desired 50% stress values may be exceeded, thus leading to the preferred properties.

The elastomer or thermoplastic elastomer of the joint spacers should preferably consist of a class of polyurethanes, and in particular of a polyurethane, polyurea or polyurethane urea.

Polyurethanes are characterized by the interplay of hard (formed from an isocyanate with low molecular weight chain) and (higher molecular weight) soft segments. Depending on their composition, polyurethanes display very different material behaviour, especially in the stress/strain curve.

Isocyanates are widely described in the literature and basically all isocyanates can be used. However, compact, slightly branched and refractory isocyanates such as Cyclohexane-diisocyanate (CHDI), Naphthalene-1,5-diisocyanate (NDI), or para-Phenylene-diisocyanate (PPDI) are preferred. Furthermore, linear, symmetrical isocyanates such as Hexamethylene-diisocyanate (HDI) are considered to be suitable. Such starting components further promote the progressive pressure-compression behaviour, resulting in the above-mentioned advantages. In addition, these isocyanates are particularly well suited to dynamic applications. The weight of these Isocyanates can be up to 50%, preferably 3%-30% of the polymers. These preferred isocyanates can also be mixed with other aromatic or aliphatic isocyanates. The aforementioned diisocyanates or mixtures of diisocyanates can also be added with polyisocyanates.

According to a preferred embodiment of the present invention, the polyurethane mixture has at least partially trans-1,4-Cyclohexane-diisocyanate (CHDI), cis-CHDI or mixtures thereof. Trans-CHDI is particularly preferable because the polymer has a particularly high crystallinity and thus obtains the preferred properties. CHDI also leads to the favoured aliphatic polyurethanes. Further, it is provided that the polyurethane mixture consists at least partially of other aliphatic isocyanates, in particular of Dicyclohexylmethane-diisocyanate ($H_{12}MDI$) or an isomer mixture thereof, or a mixture of CHDI and $H_{12}MDI$.

A series of formulations and components are specified below, all of which lead to the preferred properties advantageously.

Soft segments are of crucial importance in achieving the desired progressive pressure-compression behaviour of polyurethanes with high stress values at 50% elongation or compression, and low Shore-A hardness. Preferably suitable for joint spacers are hydrolysis-resistant and bio-stable soft segments based on polyolefins, particularly polyisobutylene (PIB) or polybutadiene (PB). Furthermore, the soft segments of polycarbonate (PC) and polydimethylsiloxane (PDMS) base are valid as relatively resistant to hydrolysis. Typically known in the literature or commercial, also medical polyester or polyether urethanes are not sufficiently biostable for long-term implants and are therefore less suitable or are not preferred, even if they can be blended in relatively small amounts. Silicone-ether-polyurethane copolymers too appear to have inadequate biostability.

According to a preferred embodiment of the present invention, the soft segment of the elastomer or thermoplastic elastomer is a polyisobutylene (PIB) or a bifunctional polyisobutylene, preferably a hydroxyl-terminated (HO-PIB-OH) or an amine-terminated ($H_2N$—PIB—$NH_2$) polyisobutylene.

In another preferred embodiment, the soft segment is polybutadiene (PB), preferably OH-terminated and particularly preferably OH-terminated hydrogenated polybutadiene. However, amine-terminated polybutadienes can also be used.

The advantageous properties of the polymer are particularly high when the soft segment is composed solely of a PIB or PB or from a mixture of these two soft segments.

For amine-terminated PIB as the soft segment chain extenders like Ethylenediamine (EDA), or 1,4-Diaminobutane (BDA), and preferably 1,6-Diaminohexane (HDA) or 1,8-Diaminooctane (ODA) are suitable. The hydroxyl-terminated PIB can be combined particularly well with the chain extender 1,6-Hexanediol (HD). Using these chain extenders each soft segment can be mixed very well with other soft segments to modify and adjust the specific material behaviour. Preferably $H_{12}MDI$ is used, but the mentioned other isocyanates can also be used.

The hydroxyl-terminated PIB also gives a suitable polyurethane with the chain extender butanediol if the catalyst 1,3-Diacetoxy-1,1,3,3-tetrabutyldistannoxane (DTDS) is used. In this case, the polymer can also be synthesized in a 1-step polymerization process, without the so-called prepolymer, which is otherwise used in the two-step procedure preferably. Besides the preferred isocyanates, 4,4'-Diphenyl-methane-diisocyanate (MDI) is also particularly suitable as isocyanate.

The soft segment PB, in particular the hydroxyl-hydrogenated Polybutadiene can be preferably combined with the chain extenders N,N-Diisopropanol aniline (DIPA) or 2-Ethyl-1,3-hexanediol (EHD), but also 2,2,4-Trimethyl-1,3-pentanediol (TMPD) or 2-Butyl-2-ethyl-1,3-propanediol (BEPG) work. These chain extenders can be used to mix the soft segment with other soft segments. MDI is preferred here, but the other mentioned isocyanates can also be used.

Polyurethanes are also particularly well suited and lead to the advantageous material properties, if the catalyst 1,3-Diacetoxy-1,1,3,3-tetrabutyldistannoxane (DTDS) is used for polymerization. Here, as stated above, the 1-step polymerization process is ideal.

The polyurethane types may also be cross-linked. Water is most suitable in this regard, for achieving the desired properties. Other cross-linking reagents such as 3-valent glycol or other polyvalent materials known in polyurethane chemistry can also be used.

Preferred isocyanates for water cross-linking are HDI, NDI, PPDI or CHDI. In addition to the afore-mentioned preferred soft segments PIB and PB, a preferred soft segment is polycarbonate diol (PCD) and also where appropriate, chain extender butanediol (BD) or one or more other chain extenders. The use of chain extenders however is preferably avoided, and only water is used for cross-linking.

In polyurethanes based on polycarbonate diols, polyhexamethylene carbonate diol ($C_6$-PCD) is generally used in medical technology. These consist exclusively of six methyl groups ($CH_2$) each. However, to achieve softer polyurethanes, and also at the same time to achieve the advantageous material properties which are well suited for joint spacers in particular, polycarbonate-copolymer types (polyalkylene carbonate diols) are used instead of a homogeneous $C_6$-PCD, which are built of the units hexane ($C_6$) pentane ($C_5$), butane ($C_4$) or propane ($C_3$). The copolymers preferably consist of combinations with $C_6/C_5$ or $C_6/C_4$ or $C_4/C_3$ units, expressed by the formula

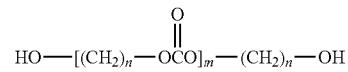

where n=6 or 5; or n=6 or 4; or n=4 or 3. In addition, the copolymer types with a decreasing number of methyl groups display significantly better abrasion resistance.

A preferred formulation, therefore, provides that the polymer of the joint spacers contains polycarbonate diol copolymers at least partially.

Particularly preferred components of the polyurethane system are, as already stated, the isocyanates HDI, CHDI, PPDI or NDI, as well as polyolefins, preferably PIB or PB and PCD as soft segments, where the above-mentioned polycarbonate diol copolymer types are preferably used for PCD. The polyolefin grades PIB or PB can be mixed or blended especially with the PCD to achieve highly abrasion resistant polyurethane types here. The proportion of PCD of the total soft segment is up to 80%, preferably 5 to 40%. The soft segments may also be mixed with other known soft segments in particular polydimethylsiloxane (PDMS) or polytetramethylene oxide (PTMO). Also suitable for achieving the advantageous properties is the addition of polydimethylsiloxane polycaprolactone block copolymers. The proportion of these soft segments in the total soft segment share is up to 50%, preferably 3 to 35%.

A further advantageous formulation provides that the polymer of the joint spacers contains only hydroxyl- and/or amine-terminated polyisobutylene, and/or hydroxyl- and/or amine-terminated and hydroxyl-terminated hydrogenated polybutadiene and/or polycarbonate diol as soft segments.

The aforementioned amine- or hydroxyl-terminated PIB may also be linear or branched PIBs. Copolymers such as acrylonitrile-butadiene-styrene may be used In polybutadienes.

Furthermore, the aforementioned isocyanates can be mixed with other aromatic or aliphatic or cycloaliphatic isocyanates such as 3,3'-Dimethyl-4,4'-biphenylene (TODD.

Besides, in the earlier displayed formulations, the mentioned chain extenders can also be introduced in a combination of two or more chain extenders and/or cross-linking reagents (e.g. Glycol) in the polymer synthesis.

In order to improve the tensile strength, the tear- and in particular the abrasion resistance of the used material, it is provided according to an advantageous embodiment of the invention that the material or preferred polyurethane mixture has nanoadditives which are in at least one dimension considerably larger than in the other two dimensions. Preferably, the nanoadditives are configured as disc-shaped or flat, or have bigger values in two dimensions as compared to the measurement in the 3rd dimension. The nanoadditives have a width of 10 nm to 50 nm, preferably 25 nm to 30 nm, and a thickness of 0.5 nm to 1.5 nm, preferably 1 nm. As a result, the progressive-pressure-compression behaviour is improved on one hand, and the tendency to creep is reduced on the other. In nanoadditives having the specified dimensions, the material does not harden, the Shore-A hardness remains almost constant, which is desirable because of the required compliance/damping of the joint spacer. However, the addition of nanoadditives increases the 50%-tensile- or compressive stress values of the polymers. The nanoadditives are preferably added in volume concentrations of less than 10%, preferably less than 5%, still more preferably less than 3%. Suitable materials of the nanoparticles are especially layered silicates, various metal oxides, carbon or Bornano particles, in addition, titanium, platinum, silver or gold particles. However, carbon nanotubes or other fibrous nanoparticles can also be added. Furthermore long-fibre reinforcements can be integrated in the material of the joint in principle.

In the previously identified embodiments of the material, 50%-tensile stress values can be achieved up to 20 N/mm$^2$ in the above-mentioned Shore-A hardness ranges, i.e., depending on the exact composition of the individual components of the polyurethane system and/or the addition of nanoparticles.

To improve the sliding properties or to reduce the coefficient of friction, it is provided that the polyurethane mixture can furthermore also have polyvinylpyrrolidone (PVP), polyvinyl alcohol (PVA) or other hydrophilic polymers or other suitable substances. The proportion of these substances is less than 10%, preferably below 3%.

In a further embodiment of the present invention, and in order to improve the progressive pressure-compression behaviour of the material, the polymer, or polyurethane mixture used can have a foam- or porous structure, wherein preferably the material after conditioning has the aforementioned stress values at 50% elongation or compression in the relevant Shore-A hardness ranges. The porous structure can in principle be open-pored in the essential form of a honeycomb, or be a closed porous structure like a classic bubble or foam structure. Tests have shown that pore sizes in the 200 μm range, as they often occur for example in polyurethane foams, damage the joint spacers relatively fast. Pores smaller than 5 μm and nanoporous structures are much better. Thanks to the water or synovial fluid absorption by the pores, even weaker materials that do not satisfy the above-mentioned parameters are fortified and can thus withstand greater loads. In principle, closed cell foam structures are advantageous from the viewpoint of durability, but mixed-cell structures have the advantage that these can absorb liquids and facilitate fluid exchange between the cells.

The joint spacer therefore has at least partially a foam structure with pore sizes between 0.1 nm to 2 μm, preferably between 1 nm to 500 nm and more preferably between 5 nm to 200 nm. Pores bigger than 2 μm, especially 5 μm usually lead to premature wear or damage to the joint spacer material. In addition, open pore structures of pore size less than 100 nm to 200 nm in particular retain components such as proteins of the synovial fluid in order to avoid a hardening or calcification of the structures. The porous structure also has the advantage that due to the liquid absorption in the pores, a supporting film (fluid friction) can build up on the surface under load. In other words, a lubrication deposit can take place in porous substrates. The joint spacer should therefore preferably be porous at the surface. However, the joint spacer can also be laminated, i.e., not have pores on the surface. To improve the sliding properties and to achieve a good fluid friction value, it can also be wholly or partially porous or roughened only at the surface.

The substances mentioned above to improve the sliding properties or to reduce the coefficient of friction, such as polyvinylpyrrolidone (PVP), polyvinyl alcohol (PVA) or other suitable substances can also be used to fill the pores of the foam structure or at least to achieve a lubrication deposit through wetting.

As described above, nanoparticles and porous structures improve the progressive pressure-compression behaviour. Moreover, the achieved effects are reinforced by combining pores and nanoparticles, particularly high 50%-tensile- or compressive stress values can be achieved at low Shore-A hardnesses.

Another embodiment of the invention for achieving the desired advantageous material properties provides for a porous non-woven structure or in particular nano-non-woven structure preferably consisting of fibres having a diameter of 0.1 to 0.4 μm. The material has a fine fibrillary structure (random non-woven) of fibres, which are preferably woven and are joined and fused together at their intersections. Furthermore, the pores of such a non-woven structure should preferably be less than 5 μm and particularly preferably less than 1 μm.

For completeness, it should be added that the progressive pressure-compression behaviour of joint spacers and the mentioned Shore-A hardnesses and 50%-tensile- or compressive stresses are preferably achieved by a foam- or fleece-like structure, if the polymers used in homogeneous or compact form are significantly harder. In other words, materials or polymers having a Shore-A hardness greater than 77 or 85 may be particularly well suited for a joint spacer, if they are softened by a porous structure and thus achieve the desired Shore-A hardnesses.

In knee spacers in particular, the central region of the joint spacer is heavily loaded due to the convexity of the condyles of the femur. In literature and patents however, there is evidence of the central area being soft and the edges being hard. However, plastics tend to creep, whereby the central area of the joint spacer is "ironed" during continuous operation, i.e., becomes wavy in the centre or develops folds, which may result in distortions and dislocation of joint spacers. In addition, the border areas can absorb less and less load over time. To achieve a joint spacer with the preferred damping characteristics (compliance), a further embodiment of the invention provides for the use of a preferably harder material for the central region and a softer material for the edges of the joint spacer. The meniscus spacer is designed such that the softer border areas are loaded first through the femur, and the harder central areas are loaded only thereafter, whereby the desired progressive compression pressure behaviour is achieved. The femoral side of the meniscus spacer has a more concave shape than the convexity of the femur, i.e., during contact, the femur touches the edges of the meniscus spacer first.

Here, the above-mentioned harder or softer materials with the corresponding 50%-tensile- or compressive stress values are used preferably. This variant can also be designed from known polyurethanes. As hard material with preferably the Shore-A hardness range between 78 to 85 one can use a material with the lower 50%-tensile- or compressive stress values of the Shore-A hardness range up to 77. In addition, as soft material, one can use a material with lower 50%-tensile- or compressive stress values than the mentioned of the Shore-A hardness range 20-77. Preferably, the soft portions extend in a wedge shape from the edge of the meniscus spacer in the middle, and are embedded on both sides of the hard material, whereby only the hard material is present centrally. The deformation of the soft edge areas and thus the preservation of recovery of these areas is limited by the central hard portion, which receives the full load.

Furthermore, the joint spacer may have a layered structure with at least three layers, namely two cover layers and an enclosed core layer. In this context the core layer and the cover layers may be made of different hard materials, preferably wherein the core layer is comparatively harder and the covering layers are relatively softer. The relatively soft edge areas preferably have appropriate thicknesses such that these areas are loaded by a condyle first so that the joint spacer initially exhibits an exceptional high degree of compliance. With increasing compression of the flexible boundary areas, the joint spacer responds more stiffly due to the relatively harder core layer (progressive pressure-compression behaviour).

The difference in the Shore-A hardness between the cover and the core layers is greater than 5, preferably between 10 and 25. The harder core layer preferably consists of a polymer having a Shore-A hardness from 78 to 90, preferably from 80 to 84. In contrast, the cover layers have a Shore-A hardness between 20 and 77 and preferably between 40 and 70. The hard and soft layers have 50%-tensile- or compressive stress values as described in the previous embodiment with a soft edge.

One of the two soft layers, in particular the distal layer—in the case of knee spacers—of the tibia (shin bone) can also be dropped, preferably if the knee spacer is fixed on the tibia. The advantage of the additional soft layer however, is that it can adapt to the individual joint-topography of the patient much better. It should be noted that the progressive pressure-compression behaviour can in principle also be achieved if the core layer is soft and the cover layers are hard.

Especially in the case of sports or mobile patients, it is observed that the joint spacer can dislocate (luxation) and lose the optimal position in the joint. The risk is particularly high especially for joint spacers designed as knee spacers because the knee has relatively less room for adequate fixation and proper form fit cannot be achieved, unlike in a joint spacer for the femoral head. To reduce the risk of dislocation, the joint spacer, especially the knee spacer should at least partially be covered along the edge with a porous fleece layer or a tape of fine fibrillary structure. The fine fibrillary structure (random non-woven) has the advantage that the surrounding cell- or tissue structures can grow in. The meniscus spacer can therefore, particularly grow together with the capsule of the knee, and contribute to correct positioning and luxation reduction. The fine fibrillary structure preferable consists of nanofibres of diameters ≤0.4 µm or thicker fibres with average diameters of about 2 µm. The fine fibrillary surface layer may cover the edge surface of the meniscus spacer in its height fully or partially. It can be connected all-over to the edge of the meniscus spacer. Preferably however, the fine fibrillary surface layer is connected to the knee spacer only at the distal and proximal edge. The advantage here is that small relative movements, and therefore a motion compensation between meniscus spacer and grown fine fibrillary edge layer takes place, supporting the positioning of the meniscus spacer further.

According to another preferred embodiment of the present invention, the joint spacer is surrounded at least partially with a hose of fine fibrillary structure, wherein an additional fixing tape is arranged. The hose is preferably attached to the full surface of the edge of the joint spacer. The fixing tape, or just the hose or tape of fine fibrillary structure without additional fixing tape serves to connect the joint spacer to a part of the joint, in case of a knee spacer to the remaining meniscal horns or other components of the tibial plateau. The fine fibrillary structure is preferably made of the same material as the actual joint spacer, so that both are preferably connected to each other by means of a diffusion adhesive.

The fine fibrillary edge can also be used to suture the meniscus spacer to the remaining meniscus or joint capsule. Alternatively or additionally, the meniscus spacer can also have single or a plurality of small holes—preferably along the outer periphery—that run through the entire thickness of the meniscus spacer or from the tibial surface and/or the femoral surface to the edge surface. It should be noted that the fine fibrillary edge may also have other fibrous structures, such as woven or knitted structures. In addition, the threads of the suture can be passed through the fibrillary edge in the outward direction. These threads leading outwards are preferably attached anterior, to the outer edge or also posterior, and can be sutured for additional fastening of the joint spacer with the surrounding tissue structures.

According to an alternative embodiment of the present invention, it is provided to prevent dislocation that the above-mentioned hose is fastened only to the circular arc shaped outer edge, and this hose extends over the ends of the circular arc to the interior of the knee. The hose forms a C shape in the top view. Through the hose is running a flexible, high-strength fixing tape made, e.g. of fibres of an ultra-high-molecular-weight polyethylene (UHMWPE) or another polymer, e.g. a polyurethane. The fixing tape can be brought out at appropriate places in the hose or the fleece edging through openings, if the hose covers the edge surface of the meniscus spacer fully. In a variant of this embodiment of the present invention, the hose with internal fixation tape or possibly only the fixing tape is not firmly bonded to the meniscus spacer, so that the meniscus spacer is very easy to replace. After fastening the fixing tape in the C-shaped outline of the hose the meniscus spacer is inserted and in that held in the outward direction in a form-fitting manner.

Preferably, the fixing tape is attached to the remaining meniscal horns. This can be achieved by means of sewing, via self-locking clips or clamps that can be closed and then opened again, or couplings respectively. The clamps or couplings are made e.g., of a shape-memory alloy. The clamp or coupling with one half firmly connected to the tape is pressed with the other half in the knee with a pair of pliers. The clamp could in this case be equipped with claws, which can "bite" into the meniscal horns. It can be reopened through a repeat intervention by increasing the temperature above body temperature. In a preferred embodiment, the clamp or coupling made of a shape-memory alloy can also be closed through a temperature pulse (without active pressing with pliers). Another variation is one half of the coupling is fixed firmly to the meniscal horn and the other half connected to the fixing tape. After fixing the tape with the meniscal horns, the fine fibrillary material hose can be pushed over the connecting point. The hose can be designed as slotted at the ends to facilitate better guidance through the connecting point, i.e. the clamp or coupling. The slotted hose ends can be fixed (distal) again after the displacement, possibly with the help of a velcro interlock.

If fixing on the remaining meniscal horns is not possible, the tape can be fixed in the holes in the tibial plateau, wherein the holes are preferably drilled in the trough configurations (intercondylar area anterior or posterior) of the tibial plateau, more precisely at the start or end point of the front—or rear horn. For this purpose, the fixing tape may be connected at the ends with pin-shaped components via detachable clamps. The meniscus implant can also be fixed the same way.

According to a further preferred embodiment of the present invention, it is provided that the fixing tape runs in a circumferential groove in the core layer of the joint spacer and emerges from the fine fibrillary edge layer. The fixing tape is fixed in the groove preferably freely, or in the core layer. Here, the core layer of the outer edge is designed thicker, which reinforces the suspension by the fixing tape. Alternatively, the fixing tape can also be pasted only at the edge surface of the meniscus spacer or secured otherwise. The fine fibrillary fleece layer is then connected to the edge surface at the distal and proximal edge.

It is further provided in accordance with another embodiment, that the tape runs in a U-shaped or L-shaped mounting rail, so that the joint spacer is mounted as detachable from the fixing tape. Preferably, the U-shaped profile rail is connected to the core layer of the joint spacer. As the fixing tape may remain permanently in the knee according to the described fixing methods, preferably only the joint spacer must be replaced during a reoperation, while the fixing tape can remain in the patient's body.

The U- or L-shaped profile rail is preferably connected to the fixed core layer of the joint spacer and covered on the outside with a fine fibrillary structure. According to an advantageous embodiment of the invention, the profile rail is made of a particularly hard material, a high-strength plastic or polyurethane or a metal. The fixing tape lying outside the actual joint spacer and the junction with the meniscal horn can be enclosed in the fine fibrillary hose structure. The groove may also be integrated in the sandwich structure of the meniscus spacer.

The soft border running around the knee spacer, the fine fibrillary structure, the hose or the fixing tape are also suitable preferably for the attachment of markers, whereby the knee spacer or its position and movement can be visualized with the help of imaging methods. The markers may be small pins, fine threads or wires or a ferromagnetic layer which are preferably connected to the soft and extremely flexible structure of the border. The edge or the fixing tape itself can be made of an X-ray-proof or other material that is suitable for the respective imaging methods. The attachment of the marker at the border is particularly advantageous, because the deformation of the joint spacer can be hindered least by this. If the markers were to be attached directly to the joint spacer, there would be the risk of these getting detached over time due to the dynamic loads and penetrating the joint gap.

According to a further advantageous embodiment of the present invention, the knee spacer has two projections, which are arranged on the inner edge as form-fit or force-fit in the trough configurations or holes and then on the tibial plateau. These projections are (front view) L-shaped, preferably made of the same material as the core layer of the joint spacers and are connected with this material-fit. The projections or sections of the projections may alternatively also have a fine fibrillary or other suitable structure that enables suturing the projections to the meniscal horns. The projections are designed specially to run only inside and not beyond the anterior or posterior end of the tibial plateau. They prevent only a laterally outward displacement of the joint spacer, but no movement in the anterior/posterior direction. Therefore, they can also be designed elastically, so that the anterior-posterior movement of the knee spacer is supported. According to a preferred embodiment of the present invention, the ends of the projections are configured as pins and inserted into pre-drilled holes, which are formed on the trough configurations, and in that prevent a dislocation of the joint spacer. The transition of the projections to the base of knee spacer may also be rounded and integrated in its contour. The projections may be connected to the remnants of the meniscus or the cruciate ligaments, where in this case, preferably the distally directed part of the L-projection is missing or exist in significantly reduced form.

It should also be noted that the so far known methods and elements on fixing described in patent literature or state-of-the-art can also be combined with the invention.

In addition to the fixing methods described above, the shape of the meniscus spacer has a significant influence on the risk of dislocation. According to the state-of-the-art, meniscus spacers made of flexible materials are thicker at the outer edge than in the central region, because the meniscus or meniscus replacement which is arc shaped in the top view and wedge-shaped in the cross-sectional view, is integrated in the spacer. It has been established through tests however, that this form of meniscus spacer easily leads to dislocations. There are also substantially uniform thickness knee spacers as well as meniscus spacers with anchoring ribs on the tibial side of the knee spacer which reach into the corresponding cracks of the tibia or are fixed with them. To avoid or reduce the risk of dislocation, another alternative embodiment of the present invention is made thicker in the anterior and posterior than in the central area of the meniscus spacer and at least at one place of the outer edge, it has equal thickness or preferably, is thinner than in the central area of the meniscus spacer where, viewed from the centre of the circular edge contour, it extends an angle of 90°, preferably 45°. Particularly preferred is the position directly posterior to the centre of the edge. In addition, the central outer edge in the above-described area has the lowest height of the entire edge of the meniscus spacer. Of course, this shape modification can be combined with the previously described embodiments of fixing the knee spacer to reduce the risk of dislocation.

The following preferred method is applied for implantation of the knee spacer. After opening the inner space of the knee the fixing tape is connected by means of the previously described options to the tibial plateau. Subsequently, the knee spacer is inserted into the C-shaped trough built by the fixing tape. Here, the knee spacer can be threaded in its recesses (grooves, profiles) in a form-fitting manner, or just placed in the fixing tape. The knee spacer can be replaced with a new one after a definite time span. To do this, one must open the clamps described above, if necessary.

According to a further embodiment of the invention, the joint spacer is designed as a hip spacer and can be slipped over the femoral head in the form of a shell-shaped elastic coat. Advantageously, such hip spacers can be used without any bone resecting in a minimal invasive manner. Advantageously, the hip spacer—preferably in the vicinity of the proximal pole—has an opening for the execution of the femoral head ligament.

According to a preferred embodiment of the invention, the hip spacer is separated from the hole to the edge of the shell-like coat, wherein an overlapping region is provided along the dividing line. In other words, the hip spacer is separated downwards (caudal) like a "waistband vent" in order to slide the hip spacer around the femoral head, if the femoral head ligament was not separated. Preferably, the outer part of the overlapping area has a plurality of knobs on the inner side, into which the corresponding recesses of the lower part of the overlapping region can be introduced. In this case, the knobs are preferably arranged along a media curve. Alternatively, other connecting means in the form of "nipples", "studs" or push buttons, cords or other suitable devices are provided for closing and fixing, such as a velcro fastener or form-fit connections with hinged joints or snap-hooks or other snap connections. In particular, this is a so-called beveled scarf joint, as we know from woodworking joints. Also a material-fit connection by gluing or welding is possible. Furthermore, the separation of a hip spacer can be closed by tacking or with staples. A zipper or teeth of prongs is also a suitable connection. Preferably, the zipper-type connection is designed as a toothing set in the form of puzzles.

Since the hip spacer is preferably designed to be elastic, it may by slightly undersized when compared to the femoral head, so as to facilitate connection of the hip spacer to the femoral head in a form-fit and force-fit manner.

In an alternative embodiment the hip spacer can be closed proximally and designed without separation, if the femoral head ligament was separated. For this application however, the hip spacer can be separated from the equator to the free edge to facilitate being pulled over the femoral head. The separation can be carried out in the form of a simple incision or with an overlapping region in the form of e.g., the waistband vent.

The free edges of the two poles of the hip spacer can be made fully or partially of the porous fleece layer of a fine fibrillary structure. Alternatively a tape, or as in the case of the knee spacer, a hose having a fine fibrillary structure can be connected to the free edge, which extend beyond the ends of the free edge if necessary. The fine fibrillary tape itself or a fixing tape located in the hose can be used to attach the hip spacer to the femoral head neck by e.g., knotting the ends of the tape.

The materials and material structures suitable for the hip spacer correspond to the earlier descriptions of those for the joint spacer or knee spacer. In particular, the hip spacer can also be made partially of degradable materials or a matrix, which grow into the surrounding cell- and tissue structures and replace or supplement the material or matrix. The form and the concept of the hip spacer can also consist of tissue cultivating materials, i.e., produced with the help of cartilage tissues manufactured through tissue engineering.

The hip spacer—like the knee spacer—is made of homogeneous or porous material and/or has a multi-layered structure. Preferably, a sandwich structure of a harder inner core layer and softer outer layers is provided. However, one inner core layer and one soft outer covering layer can also be used. The inner side facing the femoral head can be adapted rather well to the topography of the individual femoral head patients, if it is very soft. The inner side of the hip spacer could also be attached to the femoral head with a suitable adhesive. For example, the bottom side can be sprayed with bone cement to offset the incongruencies between hip spacer and femoral head. It can also be roughened or it can have a fleece- or foam-like structure for better bonding of the inner side or inner layer. Bone structures can grow in these porous structures. The inner side therefore consists of e.g., hydroxyapatite, calcium phosphate, titanium or other suitable substance that favour a partial bone growth.

Basically, the hip spacer can be designed with the described material and sandwich structures also in the form of a socket insert, so that the hip spacer is not simply placed over the femoral head, but is inserted into the hip socket. In addition, the hip spacer can be used as a damping element for hip prostheses in the form of a coating over the head or a socket insert.

Furthermore, the material configurations and sandwich structures described in this invention can also be used for other joint spacers that can be used in other joints inside (disc, shoulder, foot and hand) or outside the human body as orthoses. They can also be used for joints of animals such as horses. In harder embodiments, the materials are also suitable for tendon or ligament replacement such as cruciate ligaments in the knee joint.

In addition, the described polymers are suitable for other implants in the human body, such as for vessels, heart valves and other valves in the human body as well as pump diaphragms and ventricles in artificial hearts and ventricular assist devices. Furthermore, they are suitable for ophthalmic implants as intraocular lenses or artificial corneas.

Figure 1C:
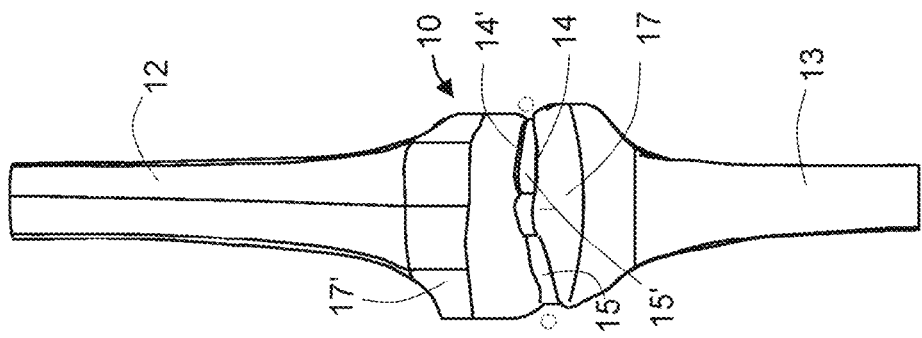
Figure 1B:
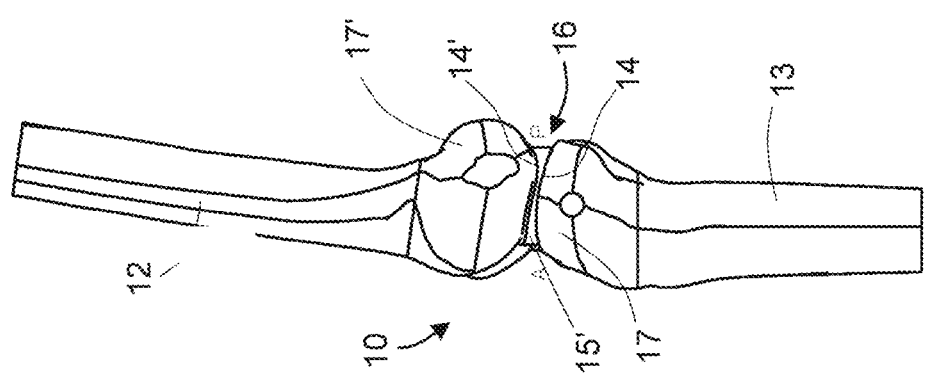
Figure 1A:
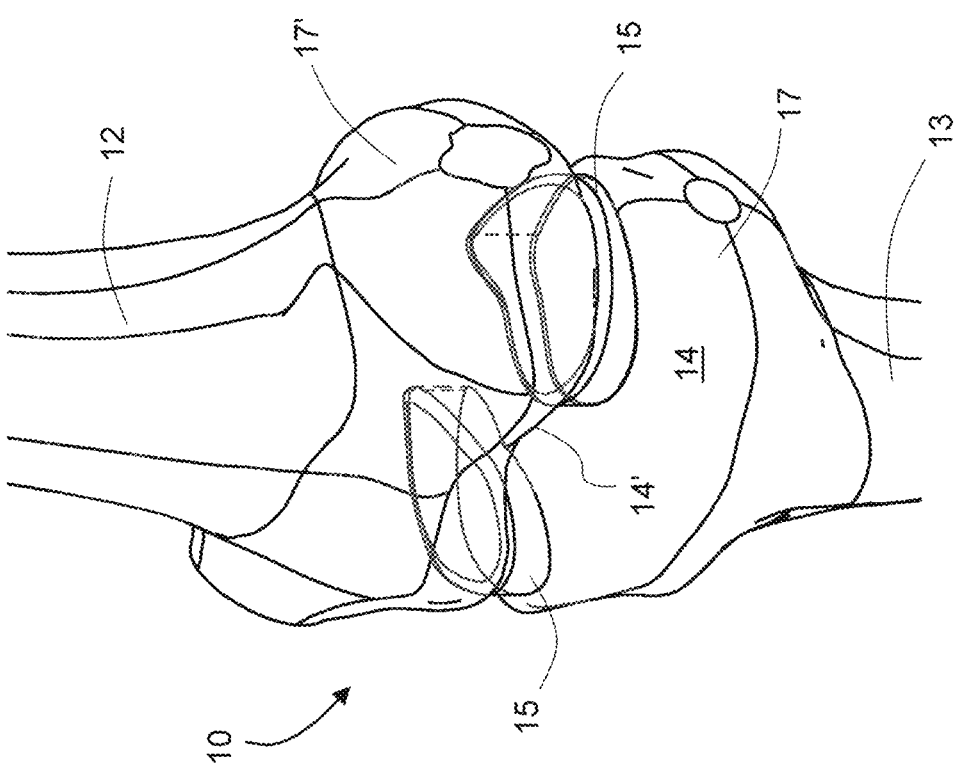
Figure 6B:
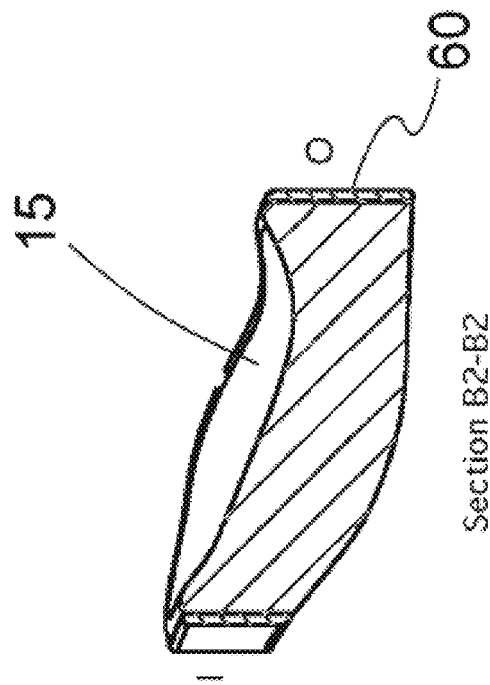
Figure 6A:
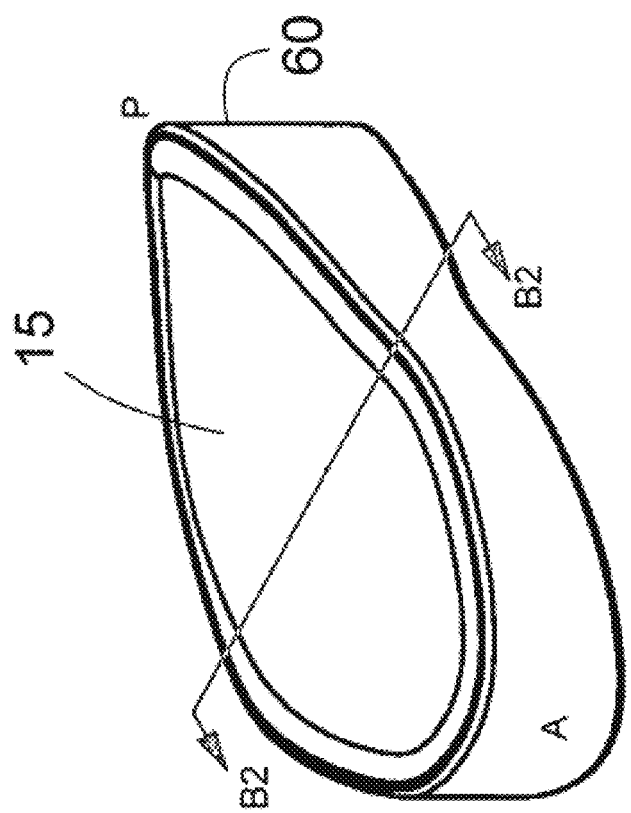

Concrete embodiments and other preferred embodiments of the present invention are explained below with the help of the figures. Shown are:

FIG. 1: Stress-strain curves,

FIG. 1a: Tibia and femur of a left knee with medial (left) and lateral (right) meniscus spacer, FIG. 1 b, c: A side view of a slightly flexed knee in lateral (b) and front view (c), FIG. 2: Top view of a left tibial plateau with the edge contours of the medial (left) and lateral (right) knee spacer, FIG. 3 a-i: Different views of a medial meniscus spacer with a sandwich structure (in load supporting condition), FIG. 4 a-i: Different views of a lateral meniscus spacer (in load supporting state), FIG. 4 j-k: Different views of the lateral meniscus spacer with a soft edge, FIG. 5 a, b: A lateral meniscus spacer with staff edge surface, FIG. 6 a, b: A medial spacer with border made of fleece-like structure (3D view (a) and sectional view (b) in accordance with Section B1-B1 of FIG. 3), FIG. 7 a-c: A medial spacer having a flat hose containing a fixing belt, FIG. 8 a-c: A medial spacer with sandwich structure, FIG. 9 a, b: A medial spacer with sandwich structure, FIG. 10 a, b: A medial spacer with a profile rail, FIG. 11: A medial spacer with sandwich structure and an open groove, FIG. 12: a, b: A medial spacer with sandwich structure having a detachable mounting rail, FIG. 13 a-e: A medial spacer with sandwich structure with projections, FIG. 14: a-e: A lateral meniscus implant with a hose in which a fixing tape is arranged, FIG. 15a-f show different viws of a lateral (femoral) joint surface spacer, FIG. 16 a, b: A lateral (femoral) joint surface spacer, FIG. 17: Shows a sectional view of a lateral joint surface spacer, FIG. 18 a-e: A lateral (tibial) joint surface spacer, FIG. 19 a-d. A hip spacer (a-b open, c-d closed), over a femoral head with a femoral head ligament, FIG. 20 a-e: A hip spacer and FIG. 21 a-b: A cross section through the hip spacer with a beveled scarf joint (A—above), an oblique section (A—below) and a plan view of a tooth in puzzle form (b) of the separated connection of the hip spacer.

The abbreviations used below have the following meaning:

a anterior p posterior

I interior-to-knee centre side of a knee spacer

O outer side of a knee spacer

FIG. 1 displays the characteristic range of tensile stress-strain curves of the preferred materials. It shows in particular the 50% tensile stress values for the materials in the Shore-A Hardness range 20-77, which should be greater than 3.8 N/mm$^2$, preferably greater than 4.6 N/mm$^2$ and more preferably greater than 6 N/mm$^2$. The FIG. 1 also displays a stress curve with a yield behaviour which should be avoided, except the yield point were to reach very high values greater than 10 N/mm$^2$. The S-curve ("S-process") illustrates that a suitable material with adequate 50% tensile stress can have much lower moduli of elasticity and tensile stress values at elongations below 50%, as in the other shown curves.

FIGS. 1 a-c show different perspectives of a (left) knee joint 10 as well as portions of a femur 12 (femur) and a lower leg 13 (tibia). Between the articular surfaces 14, 14' meniscus spacers 15, 15' are arranged, which replace the abraded and damaged (natural) meniscus. To protect the material of the meniscus spacer 15, 15', the forces to be transmitted must be spread over as large a load-bearing surface as possible. The shape, especially the edge contour of a knee spacer 15, 15' projected onto the tibial plateau 14 therefore plays a central role. The highest loads occur in almost fully stretched leg position as indicated in FIG. 1b. In this slightly flexed position, the stress in the anterior half of the knee spacer 15, 15' is at its highest due to the rising posterior femoral condyle relative to the tibial plateau 14, and the resulting expansion of the gap 16. In addition, the supporting surface of the tibial plateau 14 is narrowed down from anterior to posterior due to the trough (the posterior intercondylar area). The posterior half of the supporting surface is used especially to roll the condyles 17, 17' in more flexed positions where lesser loads occur.

Figure 2:
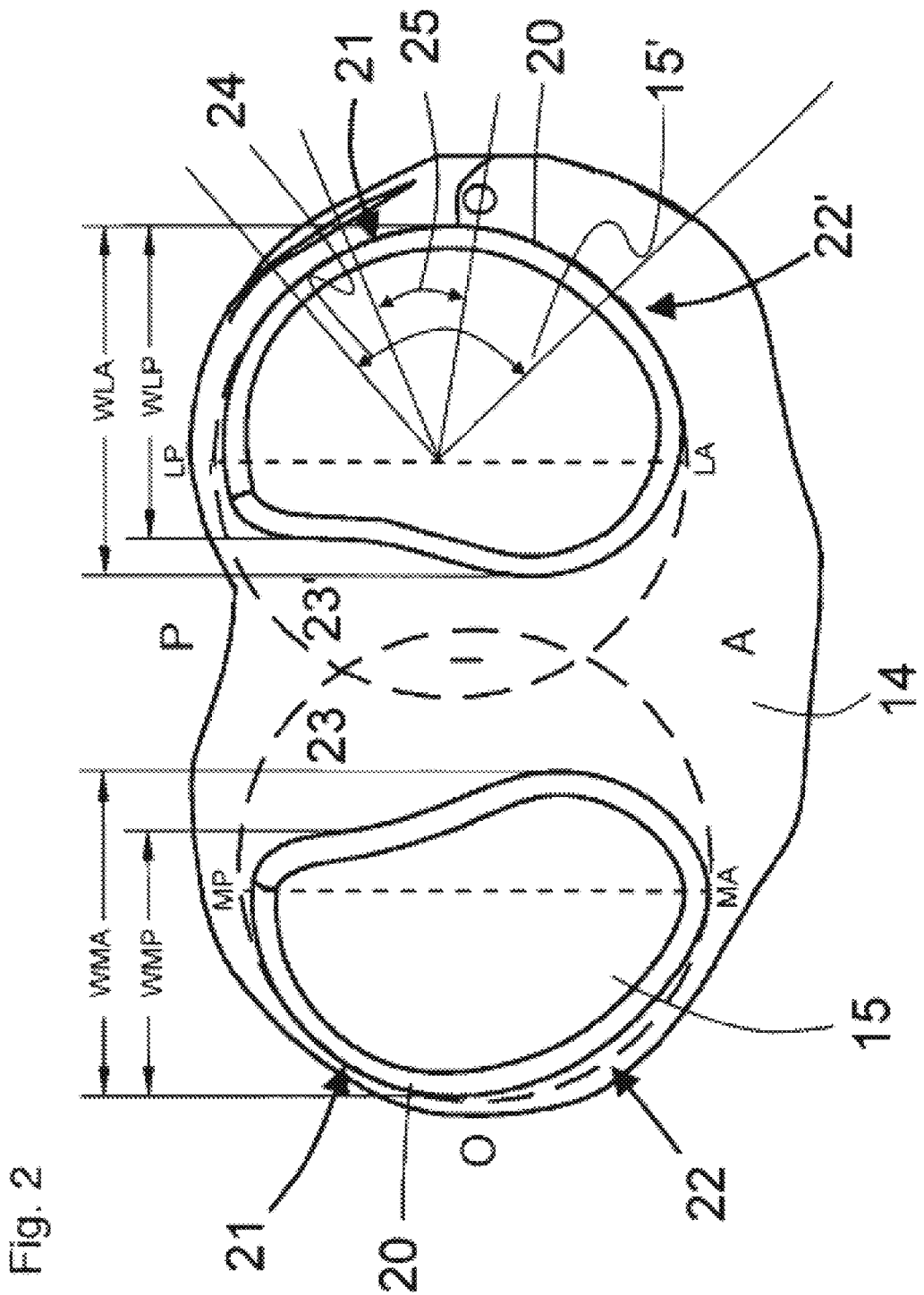

FIG. 2 shows that the edge contour 20, and thus the load-supporting border of the knee spacer 15, 15' is similar to a footprint with wider anterior and narrower posterior. In the illustrated specific embodiment of the present invention, the anterior half is wider by 10-25% than the posterior half. The outer side of the edge contour of the medial as well as lateral meniscus spacer along the anterior-posterior axis MA-MP, LA-LP is thereby configured as a substantially circular arc (arrow 21). Here, the outer side of the edge contour of the lateral meniscus spacer 15' approximates more a circular arc than the outer edge contour of the medial meniscus spacer 15 (compare Arrows 22, 22'). The inner side of the edge contour 23, 23' facing the circular arc has a concave shape from the wider to the narrower part of the supporting surface. The thus formed edge contour 21 of the medial and lateral meniscus spacer 15, 15' adapts itself to the supporting surface of the tibial plateau 14 optimally, and distributes the load to a maximum possible area. In addition, the risk of dislocation or jamming is reduced. To avoid or further reduce the risk of dislocation, the meniscus spacer 15' anterior and posterior is made thicker than the central region of the meniscus spacer 15' and at least one region at the outer edge has the same thickness or is preferably thinner than the central portion of the meniscus spacer, wherein the area seen from the centre of the circular edge contour extends about an 90° angle 24, preferably about an 45° angle 25.

The tibial surface of the meniscus spacers 15, 15' is preferably individually adapted to the topography of the tibial plateau of the patient. Alternatively, the tibial and femoral surface of the knee—the bone and cartilage of the preferred coating—is generated from a statistical 3D model of a patient group with population-specific properties. A shape model indicates the average shape of a larger number of a group with similar shapes, with which the shape variation of this group can be illustrated. Here, the patient groups can be classified according to the classification for clinical severity of arthritis, moreover the patient groups can be averaged also by gender or age-/weight groups or other criteria, such as ethnic origin. Typically, the knee shapes of an individual are created from CT or MRI images. When generating the 3D shape model, the misalignment of each of the knee shapes added in the group should be corrected to a physiologically possible alignment of the leg. In practice this depends on the individual circumstances of the patient, in this case in particular, on the ligaments or whether it is "loose" or "baggy" or "shrunk". As a result e.g., a patient with a loose ligament can be converted to a correct leg position by inserting a knee spacer more easily than in a patient with a shrunken ligament where the gap to be used for the knee spacer is too small for a normal leg alignment. The latter criteria must therefore be considered during the generation of 3D shape models in the groups to be divided, e.g., through specified degrees of misalignment of the leg.

The femoral surface of the meniscal spacer 15, 15' results from casts of the femur with angle or flexed positions (0-40°) of the femur, in which the maximum forces occur. Preferably, the impression area lies at flexing angles between 6° and 28°, preferably again in the region of the mean value of this angular range. However, the impression of the femoral side is obtained preferably from a plurality of positions of the femur or by rotating the femur within the preferred angle range, wherein the entire angular range mentioned need not be moulded. This shaping reduces the risk of dislocation considerably. The impression of the femoral side may be taken individually for each patient, or in accordance with the earlier described statistical 3D shape models. From the latter, one can derive pre-assembled or prefabricated spacers which belong to the respective 3D shape models on one hand and which are provided in various sizes and thicknesses on the other hand. The classification according to thicknesses is carried out, because non-physiological alignments of the leg (valgus/varus) or, depending on the patient and the weight and wear of the cartilage covering the knee, different joint gaps can be offset this way.

The following method is proposed preferably for selecting the appropriate thickness of the knee spacer and knee spacer shape. With one or more imaging processes the patient's leg is recorded, first in stationary condition under load where the tibia and femur are in contact and the leg has a misalignment, and then, in straightened condition with the correct leg position, in this case preferably from the front and the side view. From the second record, the resulting gap between the femur and tibia can be used to select the thickness. Preferably, however, the difference of the distance from the femur and tibia in the two images is used to select the appropriate thickness of the knee spacer. It is advantageous if this can be done in a simple and cost-effective 2D image such as an X-ray. In addition, it is also advantageous if, based on characteristic landmarks or other characteristics of the individual patient on the 2D image, a statistical 3D shape model and therefore the correct form of the knee spacer can be concluded, and thus a pre-assembled or prefabricated knee spacer can be selected. The relative position of the femur as compared to the tibia can be verified from a further lateral image under one of the aforementioned preferably maximum flexion positions of the leg, which is important for the impression and thus the shape of the knee spacer.

Figure 3A:
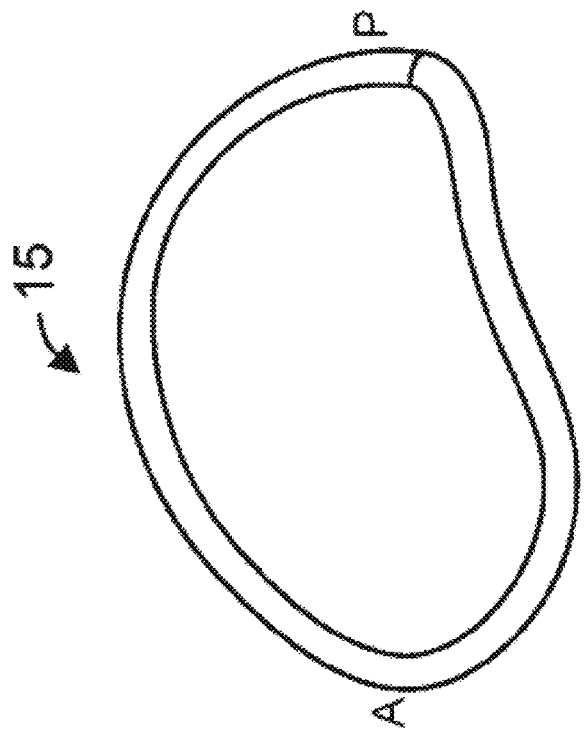
Figure 4A:
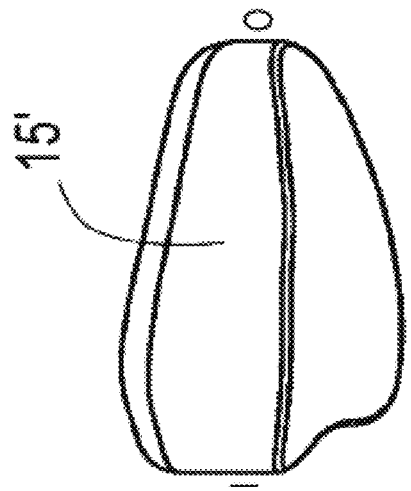
Figure 4B:
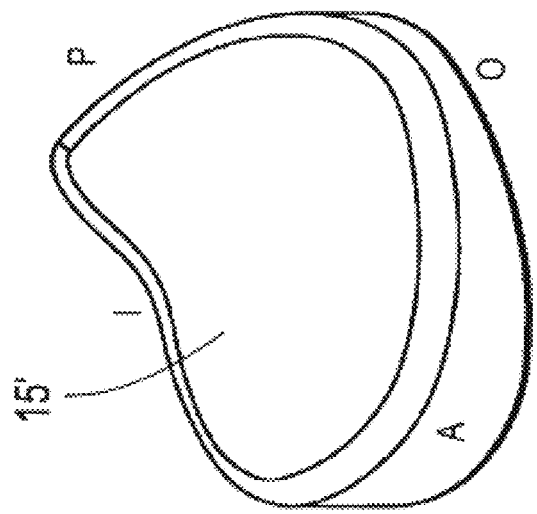
Figure 4C:
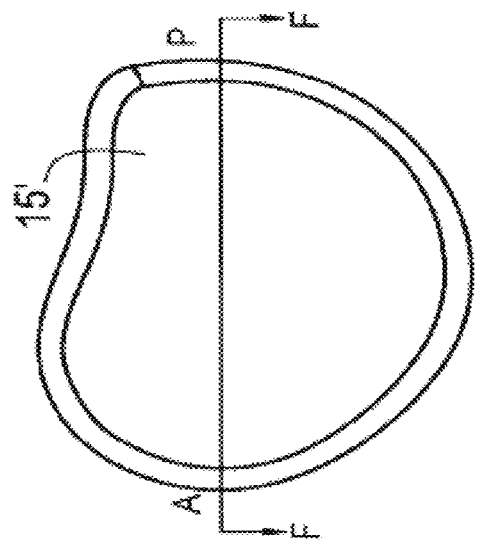

FIGS. 3 a-i show the medial meniscus spacer 15 and FIGS. 4 a-i show the lateral meniscus spacer 15'. The transitions between the edge surfaces formed by the edge contours 20 and the surfaces 31 of femoral meniscus spacers 15, 15' are rounded (Arrow 30) as the femur 12 slides over the femoral surface 31 and rolls. The transitions between the edge surfaces and the tibial surface 32 of the meniscus spacer can be rounded (FIG. 4, Arrow 40) or may not be rounded (FIG. 3, Arrow 33). The latter in particular if the meniscus spacer 15, 15' is fixed on the tibial plateau 14, and therefore no relative movement can occur between the two. It is preferable that the meniscus spacer 15, 15', however, be mobile on the tibial plateau 14.

The above-described generation of the tibial and femoral surface 31, 32 of the meniscus spacer varies the height of the lateral edge surface along the circumference. The edge surfaces in the medial or lateral meniscus spacer 15, 15' are posterior and anterior higher on an average than on the side surfaces, being highest in particular at the transition from posterior to the inner edge surface. Furthermore, the inner edge surface of the medial meniscus spacer 15 in the anterior half near the transition to the posterior half (between sections g and i in FIG. 3) is the thinnest. The tibial plateau 14 is inclined or "sloping" in this area in the medial lateral direction to the plateau level in particular the inner edge (see FIG. 1c and sectional view FIG. 3 i). The thicker the spacer is here, the greater the risk of lateral luxation due to the vertical loading direction of the spacer. In contrast, in the lateral meniscus spacer 15', the inner peripheral surface is higher, or depending on the wear in valgus position and flattening of the tibial plateau 14 approximately of the same height as the outer edge surface. The lateral tibial plateau 14 has a concave shape and is arranged substantially perpendicular to the leg axis (not sloping), whereby the resultant force vector is largely coaxial with the vertical position of the legs, so that the risk of lateral dislocation of the lateral meniscus spacer is less.

In FIGS. 4 d and i is characterized the thinnest point or minimum height 41 of the outer edge, wherein at the same time, the thickness at this point is equal to or preferably less than in the central area.

The tibial surface 32 of the meniscus spacer 15, 15' is substantially convex and the femoral surface 31 concave. The curvature of the femoral surface 31 of the meniscus spacer 15, 15' is preferably greater than that of the femoral condyle such that the meniscus spacer 15, 15' is stressed first at the elastic edges, which ensures high damping.

Contrary to the representations in FIG. 3 and FIG. 4, the edge surface of the meniscus spacer need not necessarily run in the "vertical" direction, but can also run along the plane formed by the leg axis and the anterior-posterior direction (sagittal plane), as shown in FIG. 5. Furthermore, from the manufacturing point of view, the border area could be aligned such that it would be easy to demould the spacer from the production tool.

On the whole through this shaping the meniscus spacer 15, 15' follows the natural knee movement, adjusts to each flexion of the joint due to the high compliance of the material as further described below and is self-centring. In normal movement one can avoid dislocations, restrictions on movement or jamming of the spacer due to an excessively high stress and possible damage to a great extent.

It has already been explained in detail that according to a concrete embodiment of the invention, the joint spacer with a sandwich structure has a progressive pressure-compression behaviour. FIG. 3 shows an example of a spacer having a sandwich structure with a core layer 34 and two cover layers 35, 35'. The tibial cover layer 35 has a uniform thickness according to a concrete embodiment of the invention. The core layer 34 with an almost constant thickness joins this cover layer 35 preferably along the entire surface. The thickness of the core layer 34 of the medial meniscus spacer 15 may become thinner however, in particular between the line MA-MP (FIG. 2, line LA in the lateral meniscus spacer) and the inner edge (see. FIG. 3 g), to ensure that the lateral luxation risk in the tibial plateau rising at the centre of the knee can be kept low. In addition, the core layer 34 does not need to extend fully to the edge of the spacer. The tibial cover layer has a thickness of about 3 mm, preferably between approximately 0.2 and 2 mm. The core layer 34 has, as a function of the total thickness of the meniscus spacer 15, 15' and the knee gap, a thickness preferably in the range of approximately 3-10 mm. The femoral cover layer 35' follows the core layer 34 on top with a non-uniform thickness distribution, which is relatively thin in the centre and with increasing thickness towards the edge. The soft covering layers 35 and 35' with their thicker edge region can damp shock loads exceptionally well. The high flexibility of the sandwich structure ensures that the meniscus spacer 15, 15' can adapt itself to knee movement during flexion and extension. This further reduces the risk of luxation.

Figure 9A:
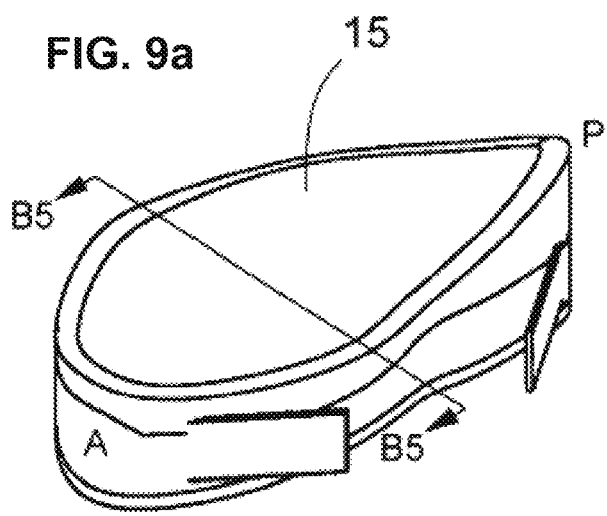
Figure 9B:
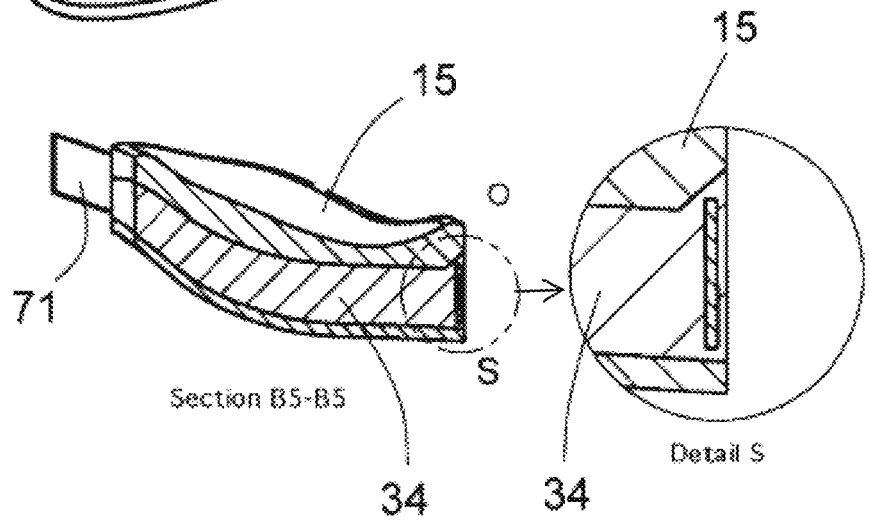

In another embodiment of the present invention, the core layer 34 of the meniscus spacer 15, 15' can be thicker towards the outer circular arc-shaped edge, e.g., if the spacer as described below for FIG. 9 b, is fixed with an additional circular tape on the tibial plateau 14. In the top view this thickening forms an additional C-shaped reinforcement of the core layer along its outer edge.

The soft outer cover layers 35, 35' of the sandwich structure of joint spacers 15, 15' preferably consist of a particularly hydrophilic and/or low-friction and abrasion-resistant material or are additionally coated with a thin layer of such a material. In another alternative embodiment, a cover layer 35, 35' has a rough surface, or is associated with a layer of e.g., hydroxyapatite, so that they can grow together with surrounding tissue structures or the bone side of the joint. The sandwich structure described above or its individual layers are preferably made of homogeneous materials. However, all or only individual layers, preferably the outer layers can also consist of the described porous structures. Furthermore, the joint spacer can also have further inter-layers to achieve e.g., a lower grading of hardness differences or to increase the range of hardness. In addition, the individual layers may not be laminar-bonded, but they may be joined together only at their edges or optionally also slideable to one another.

FIGS. 4 j-k show embodiments of the meniscus spacer where only the edge area has a sandwich structure, and the periphery of this spacer made of a harder material is, at least partially inserted a wedge-shaped ring made of softer material around the circumference. The edge portions can also be configured differently than illustrated in the figures, e.g., the soft material can be superimposed on the harder material in the edge area, or the edge is made of soft material over the entire thickness.

To reduce the risk of dislocation for sportier or more mobile patients, the edge surface of the meniscus spacer 15, 15' in another concrete embodiment of the current invention is covered along the entire circumference with a porous fleece layer 60 of a fine fibrillary structure (random non-woven) (FIG. 6) in which the surrounding cell and tissue structures can grow without forming hardening, scarred tissues. The meniscus spacer 15, 15' can thus adhere to the capsule of the knee and contribute to positioning and reduction of dislocation. According to another embodiment, it is provided that the fine fibrillary edge layer 60 is connected only at the distal and proximal edge to the knee spacer (FIG. 12b, Arrows 120, 121). The advantage here is that if there are small relative movements, a motion compensation between meniscus spacer 15, 15' and the fine fibrillary edge layer is triggered, and the positioning of the meniscus spacer is still supported. For this purpose, according to a particular embodiment, a flat hose 70 having a fine fibrillary structure is fixed on the edge surface of the meniscus spacer (FIG. 11, FIG. 7).

In an alternative embodiment to prevent dislocation, it is provided that the hose 70 is attached only at the outer arc-shaped edge, and it is extended beyond the ends of the arc to the inner side of the knee (FIG. 7). Thanks to this design, the hose 70 has a C-shape configuration in the top view. In its inside runs a flexible and at the same high-strength fixing tape. This fixing tape 71 may be led out at the corresponding points from the hose 70 and the fleece edging through openings, when the hose is placed around the full circumference of the peripheral surface of the meniscus spacer 15, 15' (FIG. 8, FIG. 11).

FIG. 8 shows an embodiment in which the fixing tape 71 extends in a circumferential groove 80 or recess to the core layer 34 and is led out from the edge of the fine fibrillay layer 60 identically as described earlier. The fixing tape 71 or reinforcing fibres of the same type and shape used here can move freely in the groove 80, but it may also be integrated in the core layer 34 and fixed, as shown in FIG. 9. There, the core layer 34 is thickened to the outer edge, thus strengthening the suspension by the fixing tape 71. Alternatively, the fixing tape 71 can be pasted only to the edge surface of the meniscus spacer 15, 15' or otherwise secured with the fixing tape. The fine fibrillary fleece layer is then attached at the distal and proximal edge with the edge surface.

In a further embodiment, provision is made that a cross-sectionally L shaped rail 100 runs around the circular arc (FIG. 10), the distal or the tibial side releases a circumferential groove 101 in which the fixing tape 71 is inserted. According to the fixing methods described above, the fixing tape 71 may remain permanently in the knee, so that during a reoperation only the meniscus spacer 15, 15' needs to be replaced. The outer area of the L-profile 100 is preferably covered with a fine fibrillary structure. The profile rail 100 is preferably connected to the solid core layer 34 of the meniscus spacer 15, 15' and is made of a particularly rigid polyurethane, a high strength plastic or a metal. The fixing tape 71 lying outside the actual meniscus spacer 15, 15' and the junction with the meniscus horn are, according to the concrete embodiment of the present invention in FIG. 11, enclosed in a fine fibrillary hose structure. According to the embodiment of the current invention, the groove 101 is integrated in the sandwich structure of the meniscus spacer 15, 15'.

Figure 12A:
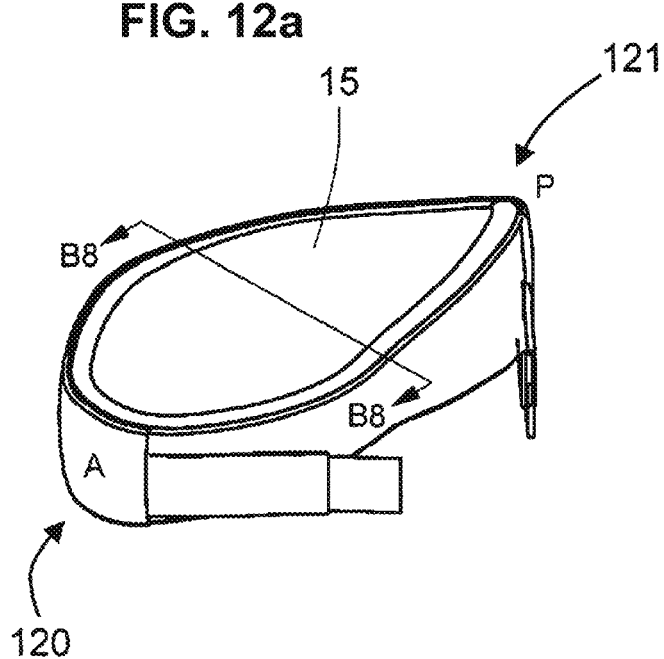
Figure 12B:
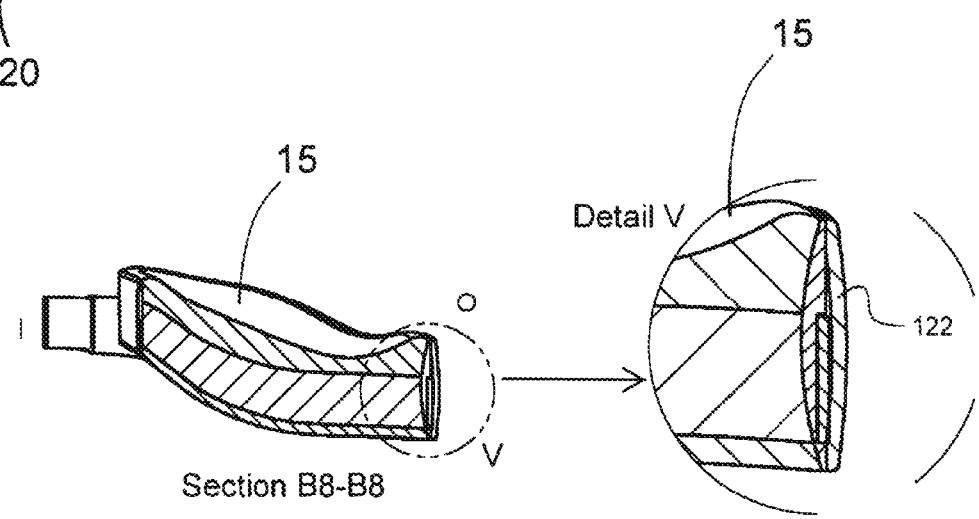
Figure 13A:
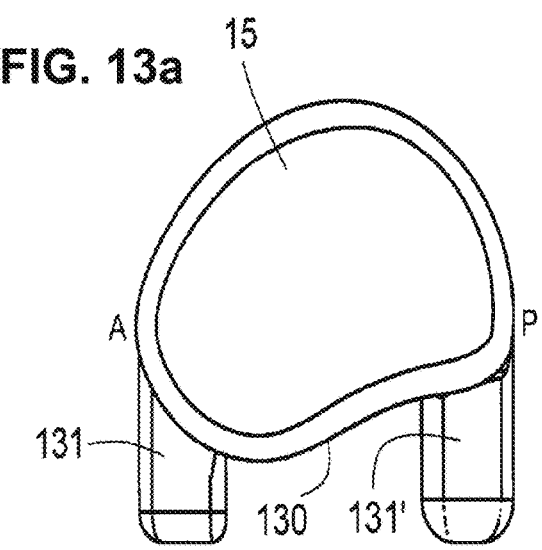
Figure 13B:
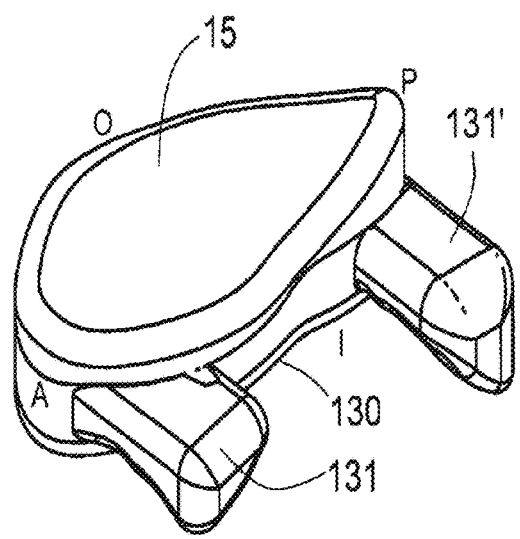
Figure 13D:
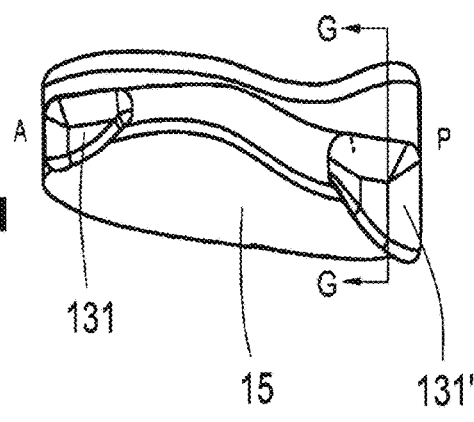
Figure 13E:
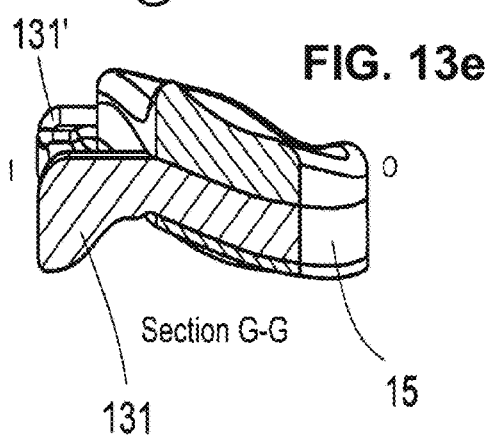
Figure 13C:
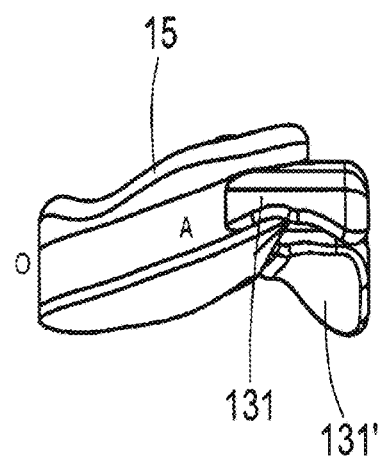

FIG. 12 illustrates another embodiment of a meniscus spacer 15, 15' with a profile rail 122, which adapts in a form-fitting manner with the edge surface of the meniscus spacer in an arc form or some other shape, but is not bonded firmly to the spacer. The profile rail 122 may also extend around the entire edge surface of the meniscus spacer 15, 15'. Thanks to this configuration, the meniscus spacers 15, 15' can be removed from the profile rail 122 and also lifted and replaced. The additional profile can be discarded in this embodiment, so that the fixing tape or possibly with a surrounding fine fibrillary hose can be placed in C-shape around the meniscus.

In a further embodiment, it is provided that a medial and lateral knee spacer 15, 15' are connected together over a one- or two-piece fixing tape 71. Here, the anterior tape end of one spacer is cross-connected to the posterior end of the other spacer. If two or possibly more than two-piece fixing tapes 71 are used the connection is established preferably through couplings or snap connections such as buckles, snap buckles, tongue and groove buckles, thus the lengths of the tapes can be adjusted simultaneously. The change in length could in this case take place by means of a separate element, e.g., an elastic band or other special clips or (clamping) buckles as used in rucksacks, suitcase belt tensioners, straps, or as a cable tie. The items listed above can also be used in the previous versions. After the coupling is actuated, the fine fibrillary structured hose could be pushed over these elements, or elements used to change the length identically as described earlier.

FIG. 13 shows another embodiment of the invention in which a meniscus spacer 15, 15', has two projections 131, 131' at the inner edge 130 and at the ends of the outer edge, which initially point inwards, and then in the distal direction 131, 131', and reach into the above-mentioned trough configuration on the tibial plateau 14 in a form-fitting manner. These L-shaped projections 131, 131' in the front view are preferably made of the same material as the core layer 34 and are connected thereto. The projections 131, 131' or sections of the projections 131, 131' may alternatively also consist of a fine fibrallary or other suitable structure which enable the suturing of the projections 131, 131' to the meniscus horns. They may also be adapted resiliently, so that a movement of the anterior/posterior knee spacer 15, 15' is facilitated. Furthermore, the ends of the projections 131, 131' can be designed as pins that protrude from the holes in the trough configurations, thus preventing dislocation of the meniscus spacers 15, 15'. The edge surface of the meniscus spacer 15, 15' is preferably covered with a layer of fine fibrillary material.

More embodiments of knee spacers are described below. FIG. 14 shows the lateral meniscal implant 140 which replaces only the meniscus in the knee. This is like the natural meniscus which is crescent shaped in the top view, and wedge-shaped cross-sectionally. The surrounding tape 141 with hose-shaped outer sheath 142 is constructed similarly to the meniscus spacer. The meniscus implant can also be combined with the other earlier-described elements for fixing and thus for avoiding luxation.

Figure 16A:
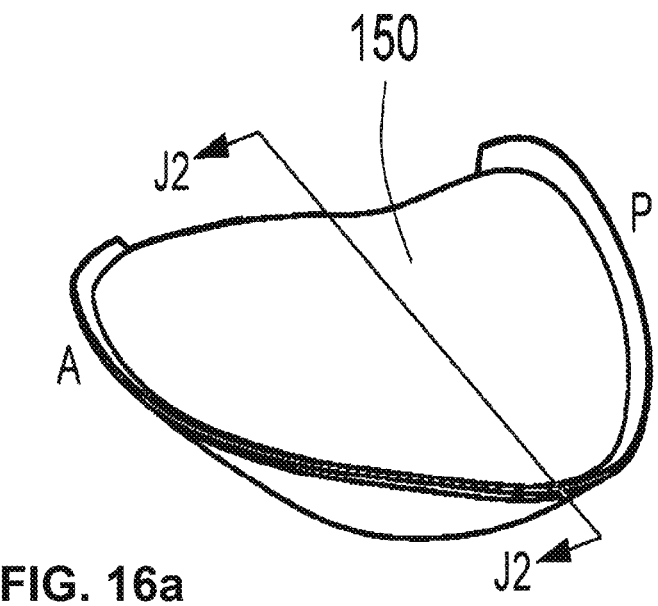
Figure 16B:
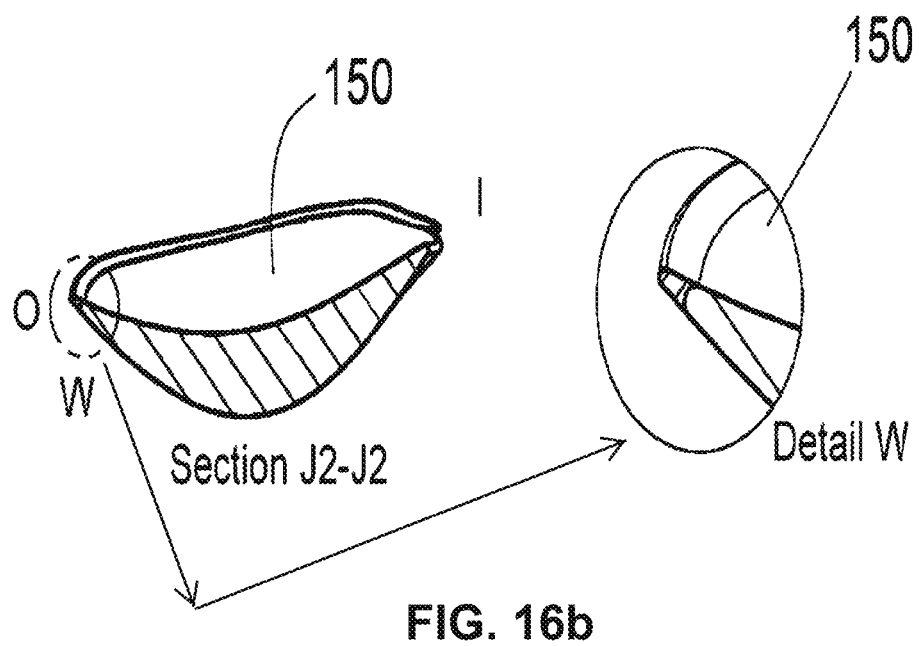
Figure 17:
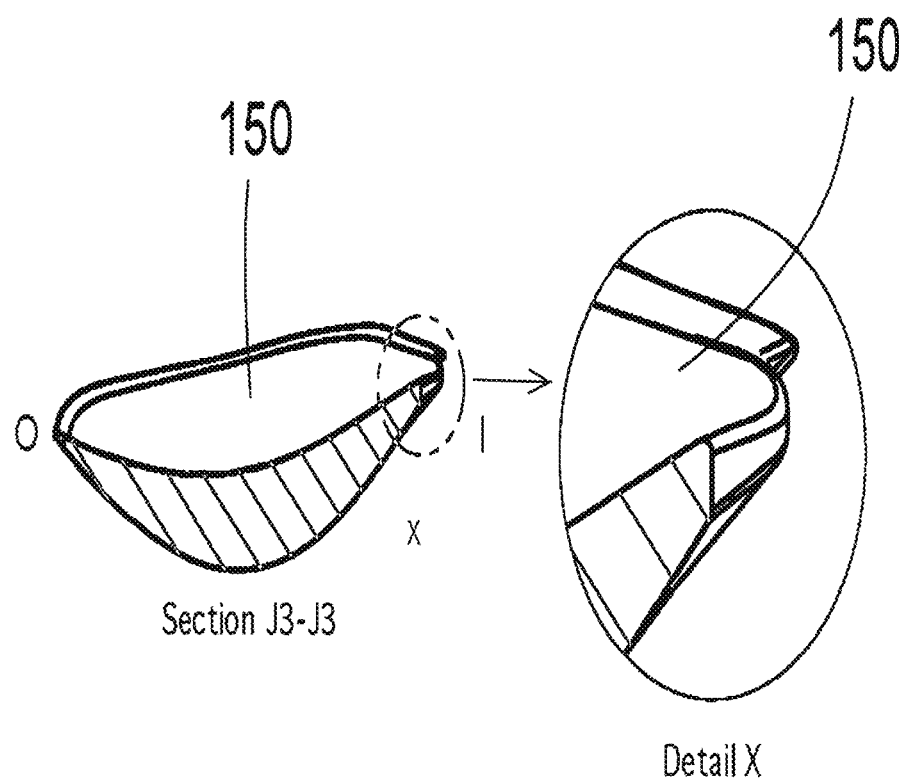
Figure 19A:
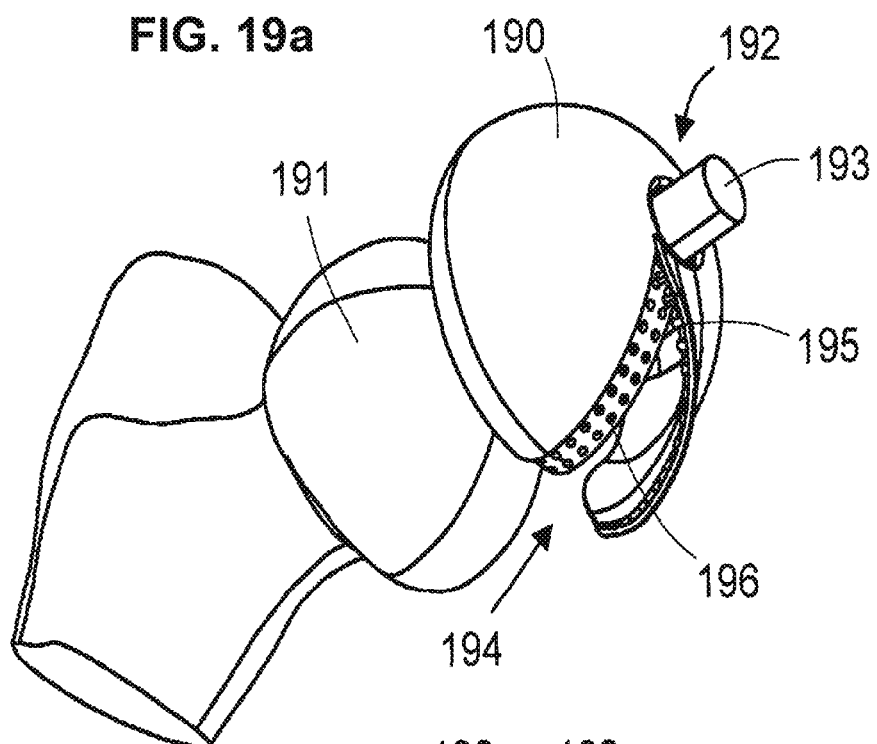
Figure 19B:
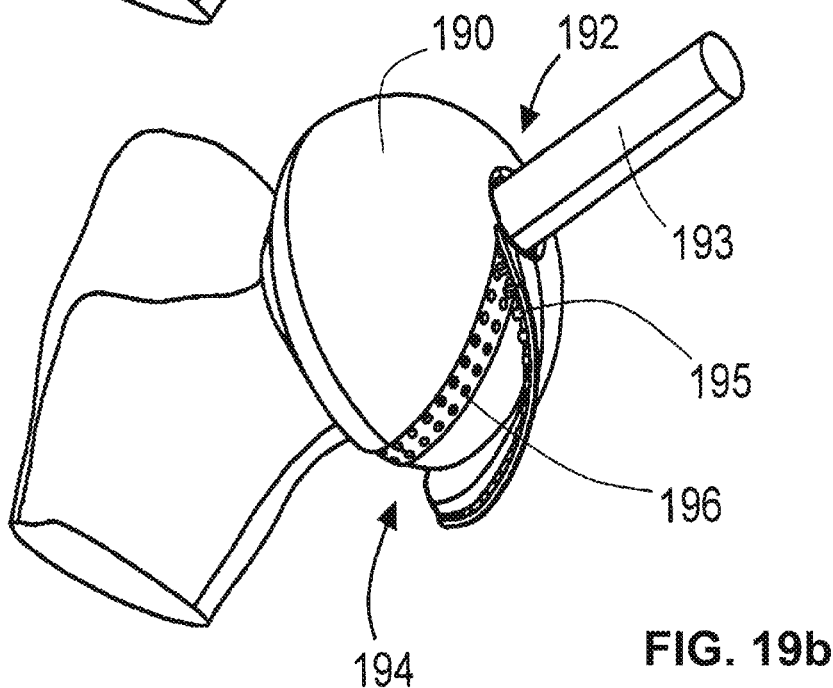
Figure 19C:
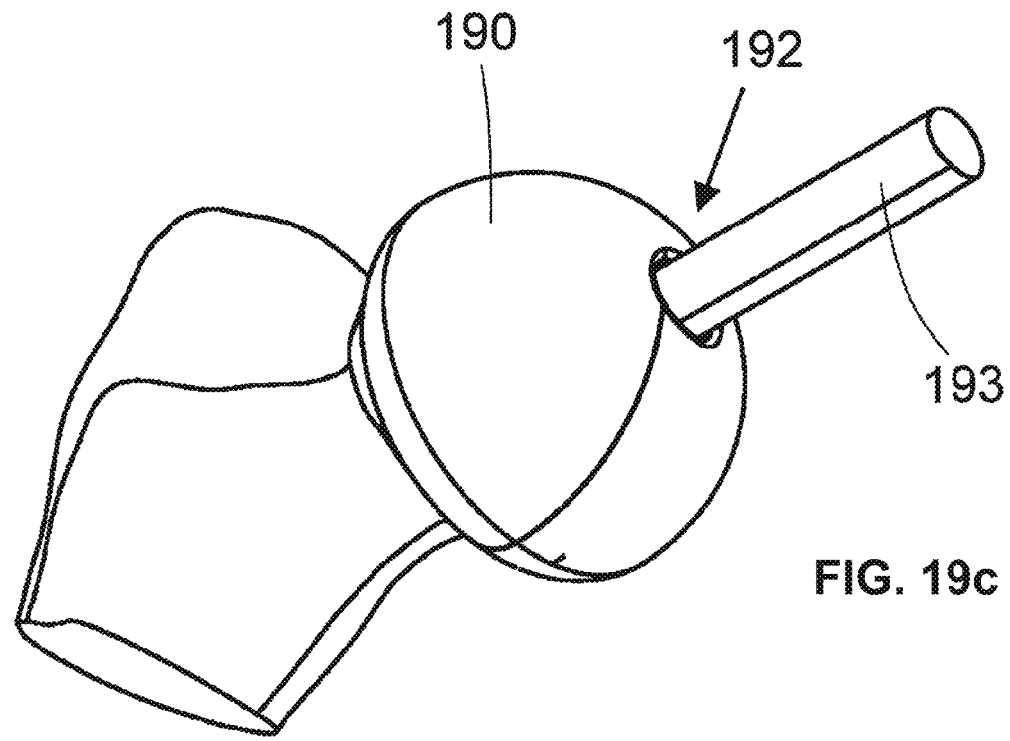
Figure 19D:
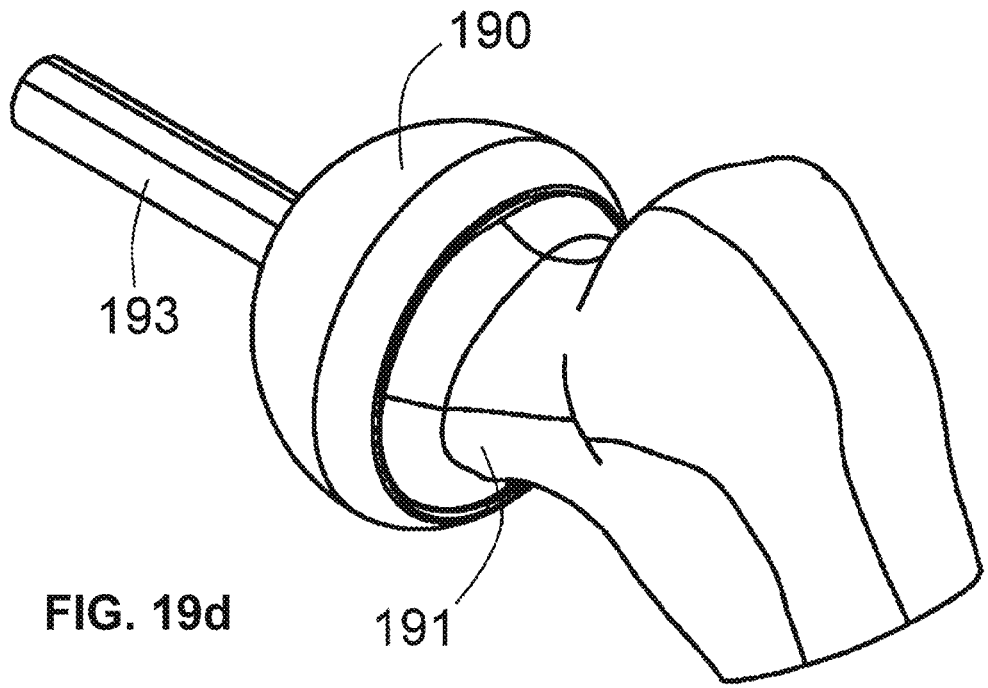
Figure 20D:
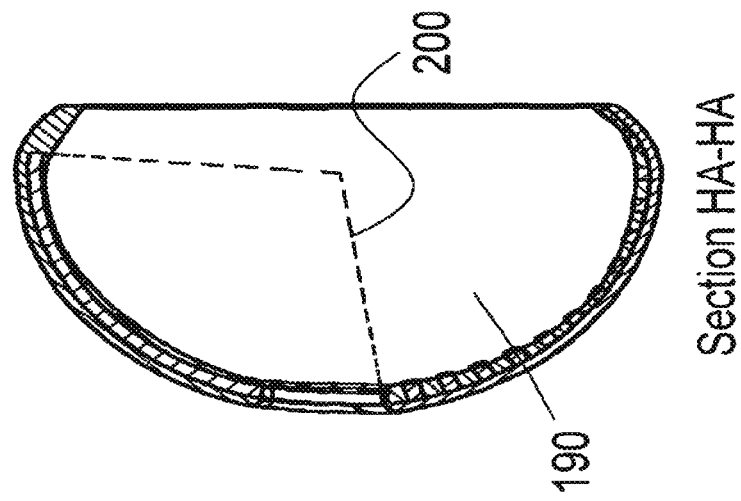
Figure 20B:
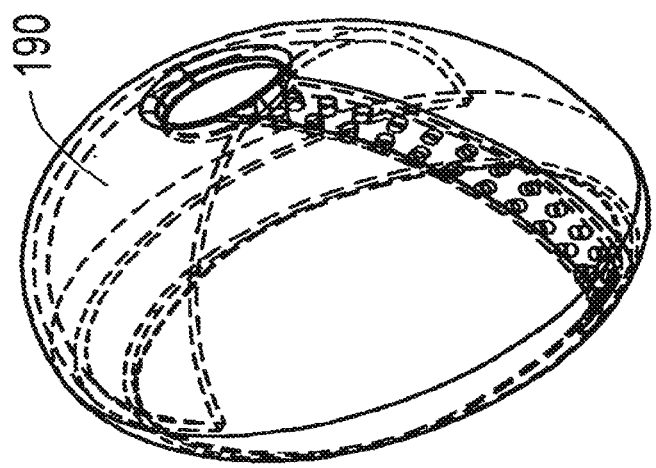
Figure 20A:
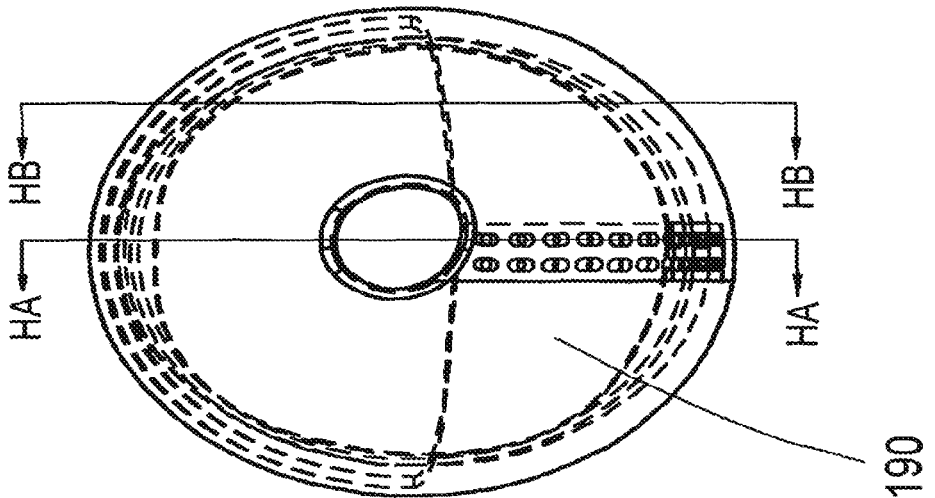
Figure 20E:
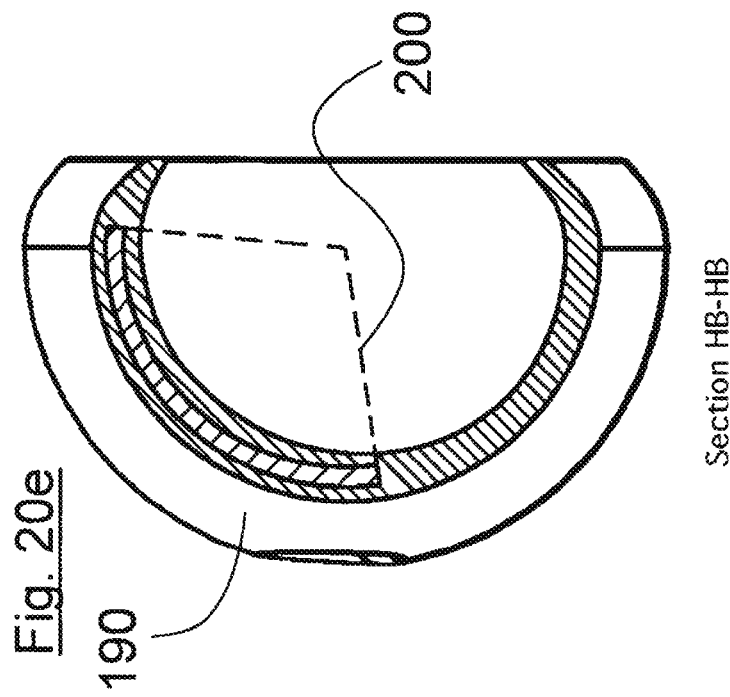
Figure 20C:
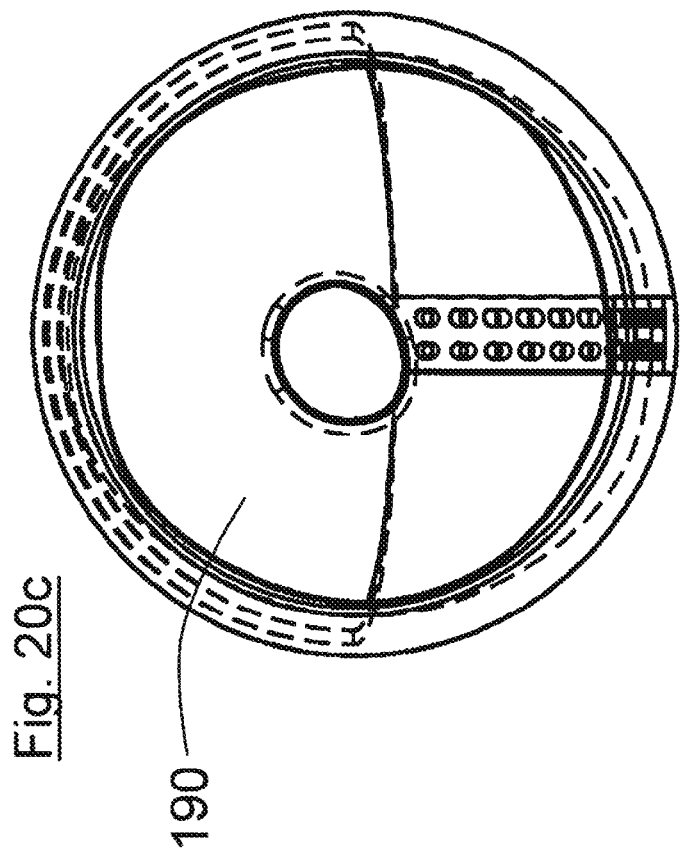

FIG. 15 shows a preferred embodiment of a lateral "femoral" joint surface spacer 150 for people suffering from osteoarthritis at an early stage, when the meniscus is still in such a condition that it must not be completely removed. The joint surface spacer 150 is placed in the concave trough of the tibial plateau 14, which is formed by the remaining meniscus in the knee. This joint surface spacer 150 is slanted towards the edge on the tibial side, so that the tibial and femoral edge contours merge. An edge surface as in the meniscus spacer does not exist. The tibial side of the femoral joint surface spacer may further comprise protrusions to fill in partially defective or partially resected menisci. However, the edge contour can be rounded (FIG. 16, detail W). In addition, the joint surface spacer can have a fine fibrillary structure (FIG. 16). Optionally, the inner edge contour can have an edge surface (FIG. 17), so that the merging tibial and femoral edge contours extend only to approx. 270°. The femoral shape of this joint surface spacer is derived identically as the femoral side of the meniscus spacer and is concave. The tibial shape is convex.

In an alternative embodiment of the joint surface spacer as "tibial", it exists essentially in a relatively flat form or as disk having nearly uniform thickness before being placed under the meniscus. FIG. 18 shows a lateral tibial joint surface spacer 180. In the medial-lateral direction however, the cross section can also be pointed wedge-shaped. The tibial surface of the joint surface spacer 180 results in a manner similar to the tibial surface of the meniscus spacer. This embodiment of the joint surface spacer can also have a fine fibrillary structure at the edge. The fine fibrillary structure enables the fixing or sewing of the femoral or tibial joint surface spacer to the upper or lower elevation with the meniscus or capsular structure. Both forms of joint surface spacers can also be used for straightening of misaligned legs (valgus, varus).

The meniscus or joint surface spacer and in particular their material embodiments and sandwich structures are suitable for appropriate shaping as a disc-shaped sliding surface for uni- or bicondylar prostheses, which usually are made of polyethylene. Particularly advantageous are the elasticity and damping characteristics of the sliding surfaces against the very hard sliding surfaces of the state-of-the-art. In case of a bicondylar prosthesis, two (medial and lateral) discs are also like an endoprosthesis connected at its inner edge. The bottom side of these plates is typically plain, it may also be different, e.g., a convex shape. For this application, the sandwich structure may be imagined as a particularly soft core layer combined with harder cover layers, the cover layers are in this case particularly slippery.

The hip spacer 190 (FIG. 19 onwards) is an elastic coating on the femoral head 191, which is preferably used in a minimally invasive way without bone and with minimal tissue resection. FIG. 19 shows schematically the application of the hip spacer 190 around the femoral head 191. The hip spacer 190 has a circular or elliptical opening 192 for the implementation of femoral head ligament 193 at approximately the proximal pole. The opening at the distal pole leads to the distal side of the femoral head 191 on the other side of the equator and to the neck of the femur. In the downward direction (caudal) the hip spacer 190 is separated similar to a "waistband vent" (Arrow 194) in order to pull the hip spacer 190 around the femoral head 191, if the femoral head ligament 193 is not separated. The thickness of the hip spacer 190 is sliced in the region of the waistband along a Meridian arc strip, preferably halved. The inner side of the outer half has a variety of knobs 195 which reach into holes 196 of the inner half and close and secure the hip spacer 190 around the femoral head 191 like a buttonhole bar. As shown in FIGS. 19 and 20, the knobs 195 are arranged in two rows along the median arc. Since the hip spacer 190 is preferably designed as very elastic, it can be slightly undersized in relation to the femoral head 191 in order to facilitate form- and force fitting fixing on the femoral head 191.

In an alternative specific embodiment the hip spacer 190 can be closed proximal and/or can also be designed without vent, if the femoral head ligament was separated earlier.

The proximal half of the hip spacer 190 is preferably spherical on the outer side and slightly deformed spherical to ellipsoidal on the inner side. Over the equator beyond the distal, the outer side of the hip spacer is ellipsoidal, and the inner side is again slightly deformed spherical to ellipsoidal, depending on the section plane. The hip spacer geometry is preferably composed of a spherical and an ellipsoidal-circular half-shell on the outer side. Diameters of samples here are 58 mm for the circular or spherical part and 32 mm for the short axis of the ellipsoid. Other absolute dimensions and diameter ratios are of course possible. The overall result is an unevenly distributed thickness of the coat, but a uniform thickness is also possible. In the case of proximal and caudal closed hip spacers, it is flattened near the proximal pole on the inner side, according to the natural flattening of the femoral head, from which the femoral head ligament comes.

The hip spacer 190 and its geometry and thickness distribution can optionally be adapted individually to the patient. This way the incongruities of the femoral head and hip socket, especially of weared sockets could be compensated better. Here too, the inner surface of the hip spacer located in the distal of the equator can vary from a circular shape so as to conform better to the neck of the femoral head (FIG. 20 c). The distal half of the hip spacer can lead to the smallest circumference of the femoral neck or complete before, as shown in FIGS. 19 and 20.

FIG. 20 illustrates the sandwich structure of the hip spacer. In order to achieve as much room as possible for congruency compensation between the femoral head and hip socket, which is preferably given by the soft material, the hard core layer can be limited to a partial surface of the femoral head, which is a particularly heavy burden. Therefore, the core layer is preferably designed in the form of a spherical lune 200. The opening angle of the spherical lune of the particularly load supporting core layer is less than 125°, preferably less than 105°. Here, the core layer extends distally beyond the equator, it begins in the proximal region of the proximal opening such that the closure bar of the hip spacer preferably consists of the softer material entirely. Thus, the pressure peaks at incompletely covered hip joints can be cushioned in particular, where the maximum pressure can be moved very close to the edge of the socket. The highly stressed parts of the joint are supported; at the same time the very soft caudal hip spacer half promotes congruency compensation.

Various embodiments for closing and fixing the separated hip spacers were described earlier. FIG. 21 shows the preferred embodiments. FIG. 21 a (upper half) displays a beveled scarf joint 211 in cross-section of the hip spacer 190, which also gives rise to an overlapping area of the separation. Instead of 2 hooks, it can also consist of only one hook. The hook blade connection 211 can also be used as a prefabricated component in the moulding process (for example in injection moulding) of hip spacer 190, through insertion into the mould cavity or subsequent pasting on the hip spacer 190. FIG. 21 a (lower half) displays a separation of hip spacer 190 in the form of an oblique section 212, the parting surfaces and the overlap region can in this case be glued or welded, for connection with the help of a Velcro fastener, using staples or several puncturing knobs. FIG. 21b displays the teeth of prongs in puzzle form (arrow 213). Thanks to the shape of the undercuts, the ends or the tines can be pushed together and need not project from above—as in an ordinary puzzle.

The invention claimed is:

1. An elastic joint spacer, to be used as a knee or hip spacer for human beings and animals, wherein the elastic joint spacer comprises a material having at least one of the following characteristics:
   a) a Shore-A hardness of 20-77 and compressive stress values at 50% compression greater than 7.8 $N/mm^2$, or
   b) a Shore-A hardness of up to 85 and compressive stress values at 50% compression greater than 10.5 $N/mm^2$.

2. The elastic joint spacer according to claim 1, wherein the material is an elastomer or thermoplastic elastomer or consists of a class of polyurethanes and whereby the elastomer or thermoplastic elastomer contains hydroxyl- and/or amine-terminated polyisobutylene and/or hydroxyl- and/or amine-terminated polybutadiene exclusively as soft segments.

3. The elastic joint spacer according to claim 2, wherein the elastomer or thermoplastic elastomer consists of a class of polyurethanes.

4. The elastic joint spacer according to claim 1, wherein the material is an elastomer or thermoplastic elastomer comprising:
   a) at least partially amine-terminated polyisobutylene as soft segment, and Ethylenediamine and/or 1,4-Diaminobutane and/or 1,6-Diaminohexane and/or 1,8-Diaminooctane as chain extender, or
   b) at least partially hydroxyl-terminated polybutadiene as soft segment, and at least partially 2,2,4-Trimethyl-1,3-pentanediol and/or 2-Butyl-2-ethyl-1,3-propanediol and/or N,N-Diisopropanol aniline and/or 2-Ethyl-1,3-hexanediol as chain extender.

5. The elastic joint spacer according to claim 1, wherein the material is an elastomer or thermoplastic elastomer comprising at least partially polycarbonate diol and/or polycarbonate diol copolymer types.

6. The elastic joint spacer according to claim 1, wherein the material is an elastomer or thermoplastic elastomer comprising one of the following substances as soft segments:
   a) polyisobutylene and/or polybutadiene, and up to 80% of a polycarbonate diol and/or polycarbonate diol copolymer type, or
   b) polydimethylsiloxane or polydimethylsiloxane or polycaprolactone or polytetramethylene oxide block copolymers, or a mixture of one or more of these soft segments, in a proportion of up to 50% of one or more of these soft segments.

7. The elastic joint spacer according to claim 1, wherein the material is a polyurethane comprising Naphthalene-1,5-diisocyanate and/or para-Phenylene diisocyanate and/or trans-1,4-Cyclohexane diisocyanate and/or Hexamethylene diisocyanate.

8. The elastic joint spacer according to claim 1, wherein the material is a cross-linked polyurethane and a cross-linking reagent used is water or water in combination with one or more further chain extenders and/or cross-linking reagents.

9. The elastic joint spacer according to claim 1, wherein the elastic joint spacer has at least one of:
   a) nanoadditives which are disk-shaped or flat, and have a width of 10 nm to 50 nm, or
   b) at least partially a porous structure with pore sizes between 0.1 nm to 2 μm, or
   c) a nano-fabric structure that consists of fibers having a diameter of 0.1 μm to 0.4 μm.

10. The elastic joint spacer according to claim 1, wherein the elastic joint spacer comprises one or more protrusions which are arranged at an inner edge of the elastic joint spacer and which can be connected to a trough in a tibial plateau through a form-fit or a force-fit, or by pin-shaped projections which can be inserted into prefabricated holes in the trough in the tibial plateau.

11. The elastic joint spacer according to claim 1, wherein the elastic joint spacer is configured as a hip spacer and can be slipped over a head of a femur and having a form of a shell-shaped elastic coat, having an opening for a femoral head ligament.

12. The elastic joint spacer according to claim 11, wherein the hip spacer
    has a separation line extending from the opening up to an edge of the shell-shaped elastic coat formed by two overlapping regions of the shell-shaped elastic coat.

13. The elastic joint spacer according to claim 12, wherein one of the overlapping regions comprises a plurality of knobs that are inserted in corresponding recesses in the other overlapping region.

14. An elastic joint spacer, to be used as a joint spacer for human beings and animals, wherein the elastic joint spacer comprises a material having at least one of the following characteristics:
    1) a Shore-A hardness of 20-77 and compressive stress values at 50% compression greater than 7.8 $N/mm^2$, or
    2) a Shore-A hardness of up to 85 and compressive stress values at 50% compression greater than 10.5 $N/mm^2$, and
    wherein:
    a) an edge zone of the joint spacer comprises a material having a Shore-A hardness between 20 and 77, and a material of a harder central area has a Shore-A hardness greater than 77 with tensile stress values at elongation between 20% and 60% greater than 3.8 $N/mm^2$, or
    b) the joint spacer has a partially layered structure comprising at least two cover layers and an intervening core layer made of different hard materials, wherein the difference in the Shore-A hardness between the cover layers and the core layer is greater than 5, and at least one of the layers is of a material with tensile stress values at elongations between 20% and 60%, greater than 3.8 $N/mm^2$, or compressive stress values at compressions between 20% and 60%, greater than 7.8 $N/mm^2$.

* * * * *